(12) United States Patent
Pickhard

(10) Patent No.: US 8,814,823 B2
(45) Date of Patent: Aug. 26, 2014

(54) METHOD AND DEVICES FOR LYOPHILIZING, RECONSTITUTING, AND ADMINISTERING A RECONSTITUTED AGENT

(75) Inventor: Ewald Pickhard, Grossebersdorf (AT)

(73) Assignee: Pharma Consult Ges.m.b.H. & Co Nfg KG (AT)

( * ) Notice: Subject to any disclaimer, the term of this patent is extended or adjusted under 35 U.S.C. 154(b) by 1183 days.

(21) Appl. No.: 11/666,263

(22) PCT Filed: Oct. 25, 2005

(86) PCT No.: PCT/AT2005/000423
§ 371 (c)(1),
(2), (4) Date: Dec. 22, 2008

(87) PCT Pub. No.: WO2006/045132
PCT Pub. Date: May 4, 2006

(65) Prior Publication Data
US 2009/0131864 A1    May 21, 2009

(30) Foreign Application Priority Data
Oct. 25, 2004    (AT) ................ A 1804/2004

(51) Int. Cl.
*A61M 37/00*    (2006.01)
*A61M 5/28*    (2006.01)
*A61M 5/24*    (2006.01)
*A61J 1/20*    (2006.01)
*A61M 5/315*    (2006.01)

(52) U.S. Cl.
CPC ....... *A61M 5/284* (2013.01); *A61M 2005/2451* (2013.01); *A61J 1/2089* (2013.01); *A61M 2005/31598* (2013.01)

USPC ................................... 604/89; 604/82

(58) Field of Classification Search
CPC ............. A61M 5/284; A61M 2005/2451; A61M 2005/31598; A61J 1/2089
USPC ................ 604/83, 89, 91, 82, 90, 92
See application file for complete search history.

(56) References Cited

U.S. PATENT DOCUMENTS 3,542,023 A * 11/1970 Ogle ..................... 604/88
4,171,698 A    10/1979 Genese
(Continued)

FOREIGN PATENT DOCUMENTS

DE    3924830 A1    2/1991
DE    41 27 650 C1    2/1993
(Continued)

*Primary Examiner* — Bhisma Mehta
*Assistant Examiner* — Jenna Zhang
(74) *Attorney, Agent, or Firm* — Lerner, David, Littenberg, Krumholz & Mentlink, LLP

(57) ABSTRACT

The invention relates to a method and a device for lyophilizing, reconstituting and administering a reconstituted substance. The device has an elongate housing having a dispensing-side front housing end and a housing end lying opposite it. A first chamber, containing a lyophilizate, is disposed in the housing in the region of the front housing end and is tightly sealed at an end facing the front housing end by a removable closure and is tightly sealed in the direction of the rear housing end by a plunger. A second chamber is provided or formed in the housing in the region of the rear housing end which is connected by at least one opening to the ambient atmosphere. This opening is closed by a membrane which is permeable to gas but not to bacteria.

43 Claims, 10 Drawing Sheets

(56) References Cited

U.S. PATENT DOCUMENTS

| | | | |
|---|---|---|---|
| 4,254,768 A | | 3/1981 | Ty |
| 4,416,984 A | * | 11/1983 | Wheeler, Jr. .................... 435/31 |
| 4,445,893 A | * | 5/1984 | Bodicky .................. 604/165.04 |
| 4,643,721 A | | 2/1987 | Brunet |
| 4,941,876 A | | 7/1990 | Meyer et al. |
| 5,281,198 A | * | 1/1994 | Haber et al. .................... 604/86 |
| 5,429,603 A | | 7/1995 | Morris |
| 5,637,087 A | | 6/1997 | O'Neil et al. |
| 5,785,682 A | * | 7/1998 | Grabenkort .................... 604/82 |
| 5,788,670 A | | 8/1998 | Reinhard et al. |
| 6,440,101 B1 | | 8/2002 | Grabenkort et al. |
| 6,641,561 B1 | * | 11/2003 | Hill et al. ...................... 604/136 |
| 2004/0116874 A1 | | 6/2004 | Lourenco et al. |
| 2005/0075602 A1 | | 4/2005 | Cherif-Cheikh et al. |

FOREIGN PATENT DOCUMENTS

| | | |
|---|---|---|
| DE | 196 38 940 A1 | 4/1998 |
| DE | 197 51 226 C1 | 1/1999 |
| DE | 696 30 444 T2 | 12/2004 |
| EP | 0664137 A2 | 7/1995 |
| EP | 1 393 763 A1 | 3/2004 |
| EP | 1 459 775 A1 | 9/2004 |
| JP | 7-213609 A | 8/1995 |
| JP | H11-502731 A | 3/1999 |
| JP | 2003-511159 A | 3/2003 |
| WO | WO 97/47343 | 12/1997 |
| WO | WO 01/00261 A1 | 1/2001 |
| WO | WO 01/26718 A1 | 4/2001 |
| WO | WO 02/072171 A2 | 9/2002 |
| WO | WO 02/072171 A3 | 9/2002 |

* cited by examiner

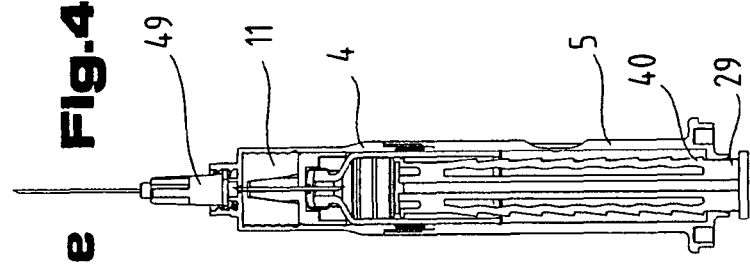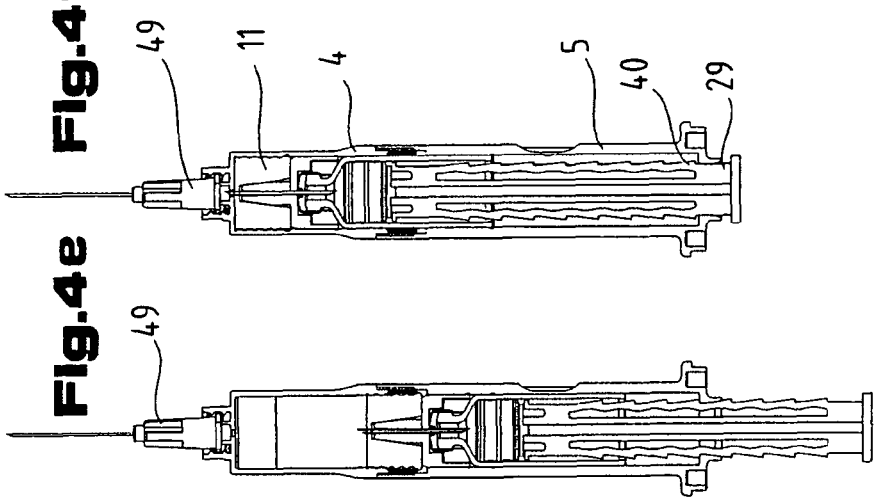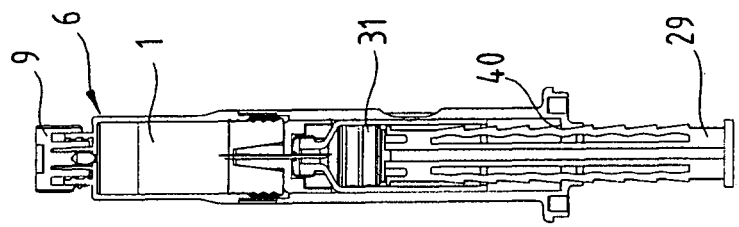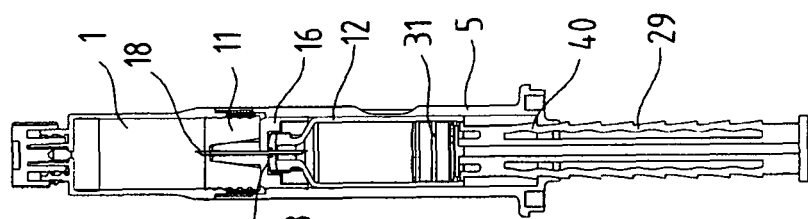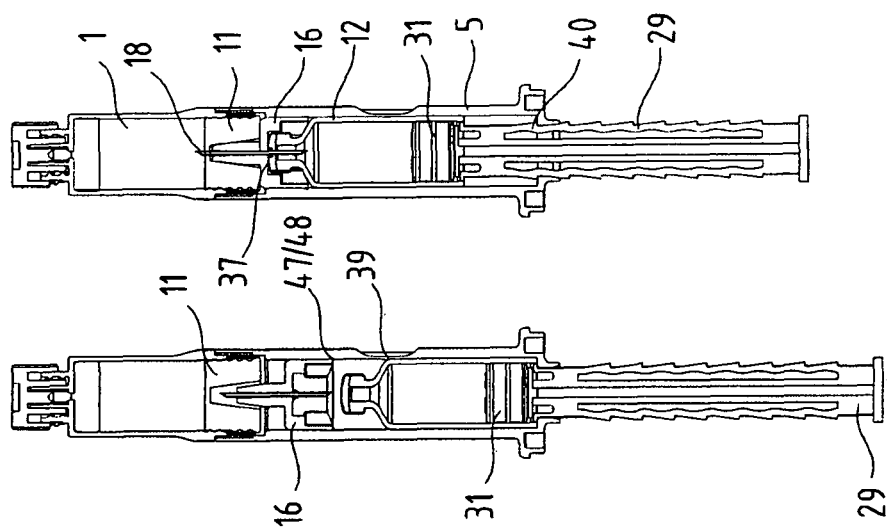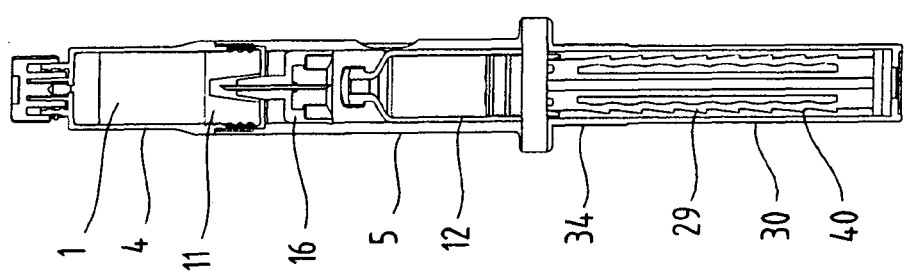

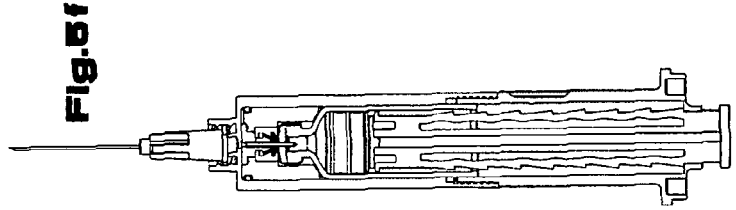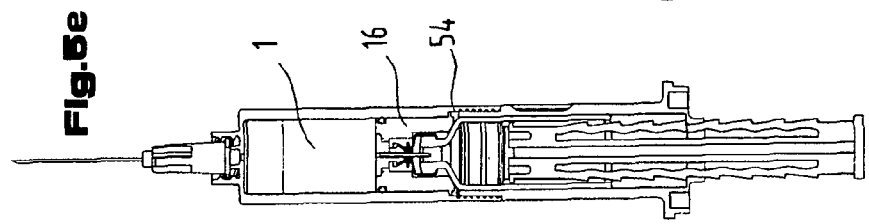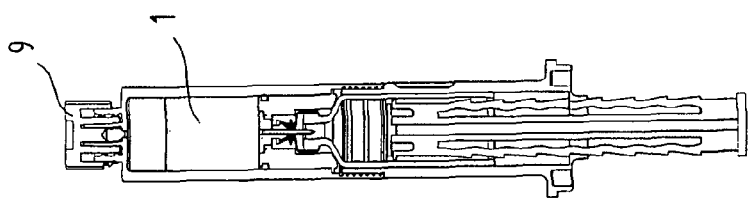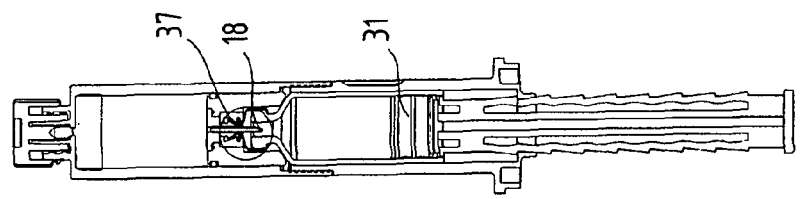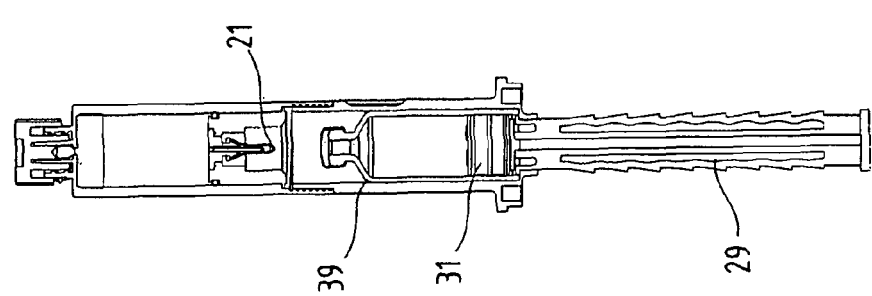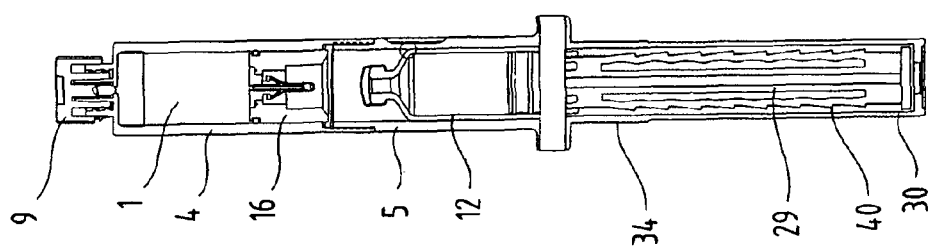

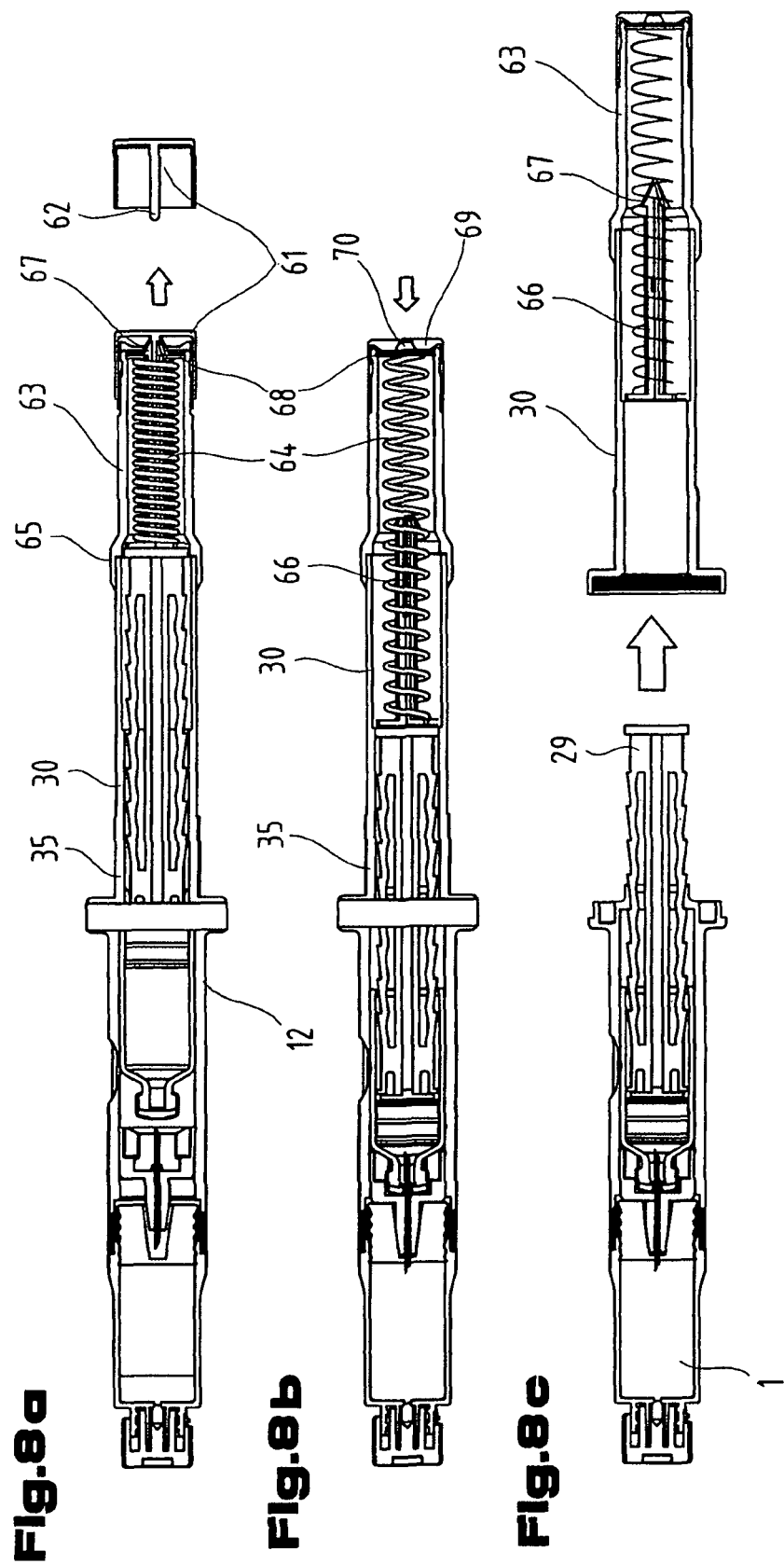

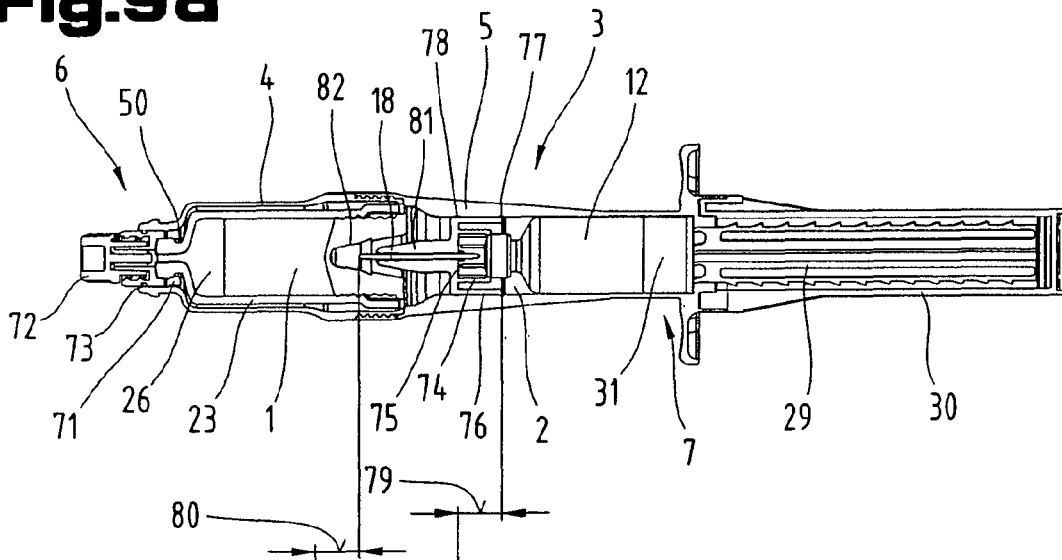
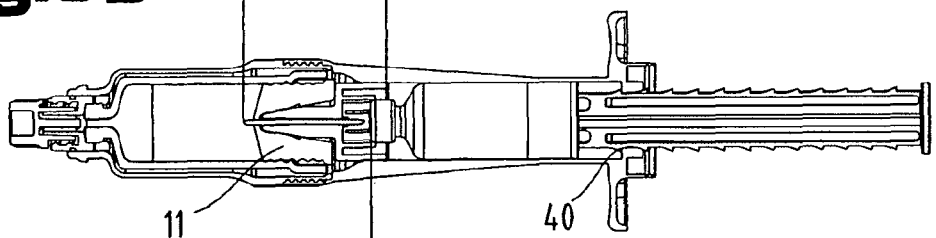
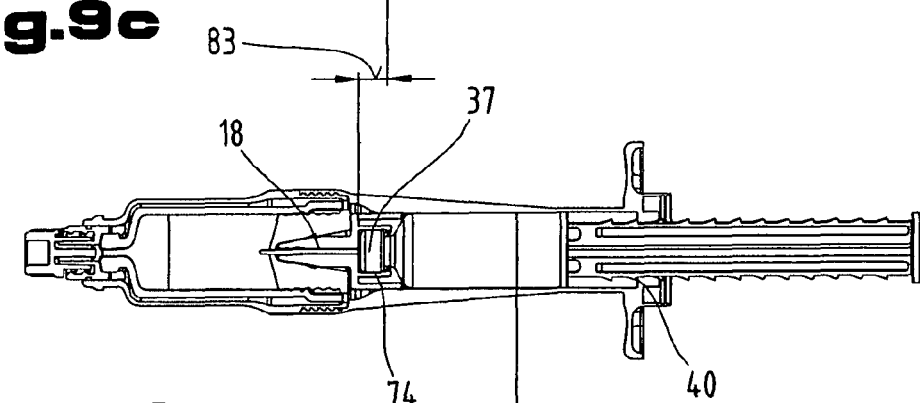
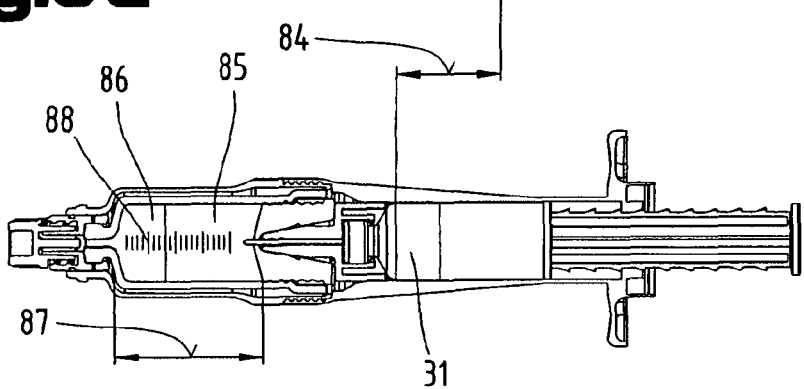

METHOD AND DEVICES FOR LYOPHILIZING, RECONSTITUTING, AND ADMINISTERING A RECONSTITUTED AGENT

CROSS-REFERENCE TO RELATED APPLICATIONS

This is a national phase application of PCT Patent Application No. PCT/AT2005/000423, filed Oct. 25, 2005 which claims priority from Austrian Application No. A 1804/2004, filed Oct. 25, 2004. The disclosure of each such application is hereby incorporated by reference in its entirety where appropriate for teachings of additional or alternative details, features, and/or technical background, and priority is asserted from each.

FIELD OF THE INVENTION

The invention relates to a method of containing, lyophilizing, reconstituting and administering substances and an applicator part or an applicator fitted with such an applicator part for a reconstituted substance.

BACKGROUND OF THE INVENTION

A method of containing, lyophilizing, reconstituting and administering lyophilized substances is already known.

For example, patent specification U.S. Pat. No. 5,637,087 A discloses a sealed first substance container containing a lyophilized substance. This substance container can optionally be inserted in an applicator together with a second container containing an injection fluid. By means of a support with a double-ended needle between the two containers which is mounted so that it can slide in the hollow barrel of the applicator, a fluid connection can be established between the first and second containers so that the fluid from the first container can be forced into the substance container under the action of a plunger also disposed in the barrel chamber of the applicator. Once the injection fluid has been forced into the substance container, the plunger can be pushed further into the cylindrical interior of the applicator to establish a line connection to an outlet which can be connected to an injection needle so that the reconstituted substance can be administered immediately it has been reconstituted. The disadvantage of this applicator is the fact that elastically deformable containers are needed and a few needle inserts also have to be provided.

DE 696 30 444 T2 also discloses the idea of using an applicator part as a housing compartment for the substance and the substance is lyophilized in this applicator part and stored in the lyophilized state.

At its output-side front housing end, this housing compartment is provided with a removable closure with a Luer lock fitting and its end remote from the front housing is sealed by means of a plunger in conjunction with an adapter inserted in it. The adapter is of a two-part design and comprises two tubular parts guided one inside the other, and the outer part is mounted so that it can slide along the internal wall of the housing compartment, whilst the inner tubular part is screwed into the outer tubular part by means of a thread and closes off an orifice in the plunger opening into the housing compartment in which the lyophilised substance is contained. The inner part can be screwed off and an injection device filled with a diluent can be screwed on instead. By forcing the injection substance out of this injection device into the housing compartment for the lyophilized substance, the latter can be reconstituted, and the outer part of the closure adapter can be moved back in the direction of the open end of the housing compartment by forcing the diluent into the housing compartment of the substance to be lyophilized, and the plunger closing the housing compartment is moved forward so that it lies against the end face of the injection device facing the housing compartment, and once the closure on the front housing has been opened and an injection needle inserted, which causes the substance in the housing compartment for the reconstituted substance to be vented, the substance can then be injected. The disadvantage of this system is that it requires the use of a separate closure adapter and the operation of removing it and inserting the injection device containing the diluent takes time.

Other pre-filled ready to use syringes containing a lyophilizate and diluent whereby the lyophilization process takes place in the syringe are known from U.S. Pat. No. 6,440,101 B1, DE 39 24 830 A1, DE 196 38 940 A1, DE 41 27 650 C1 and DE 197 150 226 C.

SUMMARY OF INVENTION

The underlying objective of this invention is to propose a device for containing, lyophilizing, reconstituting and administering a reconstituted substance, which enables the lyophilized substance to be safely stored and ensures that it can be kept sterile. Irrespective of this, the lyophilizate and the reconstituted substance do not leave the housing chamber for the lyophilized substance during the mixing operation and when being administered. Another independent objective is to ensure that the first and second housing chambers are opened and connected to the connecting element consecutively. Furthermore, the mixing operation between the lyophilized substance and diluent is independently optimized.

The objectives of the invention are achieved on the basis of the characterizing features as defined in the claims.

An embodiment of the invention provides a single device for containing, lyophilizing, reconstituting and administering a reconstituted substance, with an elongate housing composed of a dispensing-side front housing end and a rear housing end lying opposite it, and a first chamber with a lyophilizate contained in it is provided or formed in the housing in the region of the front housing end, which first chamber is tightly sealed at its end facing the front housing end by means of a removable closure and by means of a plunger in the direction of the rear housing end, and a second chamber is provided or formed in the housing in the region of the rear housing end, wherein at least one opening connects the second chamber to the ambient atmosphere and is closed by a membrane which is permeable to gas but not to bacteria. The advantage of the embodiment is provided in that the device can be closed and stored ready for use in different preparation stages but individual parts constitute a single system which can be assembled with an injection device or a dispensing device for administering the reconstituted substance with only a few manipulations. If the lyophilized substance is contained in the first chamber of the device, the number of devices which have to be retained on the mount overall can be reduced, and the other device parts are also assembled and packed in a sterilized state. This modular arrangement provides that only the device parts for the substance containing the different substances have to be stored and a smaller number of operating mechanisms with a cartridge need to be stored because they have device parts of the same type containing different substances and can be coupled immediately.

It is of particular advantage, however, if the cartridge with the liquid for reconstituting the lyophilized substance is also already contained in the sterilized and sealed container with the lyophilized substance. Thus, the cartridge containing the liquid for reconstituting the substance, the outer and inner region of the cartridge, and the chamber for the substance are thoroughly sterilized and kept so by the closure-end plunger, and the sterility is preserved even when fitted with the drive units, for example a plunger rod or an additional plunger rod housing or an auto-injector unit. Another advantage is obtained using an embodiment wherein the plunger is disposed on the side of the membrane facing the first chamber and close to it because an appropriate volume of air remains in the chamber, which, when compressed, offers an easy way of controlling the rate at which the liquid for reconstituting the substance is moved forward or compressed. This also readily ensures that the interior of the first chamber is vented when the substance is being lyophilized and the first chamber can be closed so that it is sufficiently sealed and sterile immediately after the lyophilization process in a very easy manner.

Another embodiment wherein the plunger is disposed at a distance of 0.1 to 30 mm, preferably 0.1 to 5 mm, from the membrane is advantageous because it provides a simple way of setting the volume of the air cushion in the first chamber.

Another embodiment is disclosed wherein the volume of the first chamber is greater than the volume of the lyophilized substance which enables the reconstituted substance to be used directly and the reconstitution to take place in the first chamber. More particularly, the embodiment provides a device, wherein the air pressure in the first chamber is higher than 1 bar or ambient air pressure, or wherein the air pressure in the first chamber is lower than 1 bar or ambient air pressure.

An embodiment wherein a cartridge containing a diluent is disposed in the second chamber and connection means are disposed between the first chamber and the cartridge which are designed to establish a connection between the interior of the cartridge and the first chamber, is also of advantage because the air pressure in the interior of the first chamber is defined beforehand and the mixing time and injection rate of the liquid into the first chamber can be readily set during the reconstitution process.

An embodiment wherein a cartridge containing a diluent is disposed in the second chamber and connection means are disposed between the first chamber and the cartridge which are designed to establish a connection between the interior of the cartridge and the first chamber is of advantage because the entire path followed by the substance in the interior of the device as well as the path followed by the diluent or the liquid for dissolving the substance is sterile and the connection between the chamber containing the lyophilizate and the cartridge containing the diluent does not have to be opened until the device has to be used, thereby avoiding any impairment to the sealing of closures as far as possible.

Another embodiment wherein the connection means comprise a cannula guide displaceable in the housing, in which a connecting cannula with one cannula end directed towards the piston or plunger and one cannula end directed towards the cartridge is accommodated, and the connecting cannula is a double-ended needle which can be secured by its middle region in the cannula guide and is retained by gluing, forming or by a press-fit seating, for example, has proved to be of advantage because the chamber containing the lyophilizate can be connected to the cartridge containing the diluent by means of a single connecting cannula and this connecting cannula pierces the plunger closing off the chamber and the seal sealing the cartridge.

Alternatively, another embodiment includes a cannula housed in the piston or plunger, which obviates the need for a component to hold the cannula. Another embodiment provides a configuration wherein the cannula end directed towards the cartridge is covered by means of a cap made from a rubber elastic material, so that this embodiment also guarantees sterility in the interior of the chambers.

If, as provided in another embodiment, the cannula end directed towards the cartridge is disposed in a recess of the plunger and this recess is closed off by another membrane which is permeable to gas but not to bacteria, the part of the device containing the chamber with the lyophilisate can be kept sterile even before it is assembled with the part containing the cartridge.

An embodiment may provide a first chamber in the form of a glass cylinder which is in turn accommodated in the housing. The substance or active substance can be lyophilized in this glass cylinder beforehand.

An embodiment is also disclosed wherein the glass cylinder has a tapered opening at the dispensing-side end, which supports an adapter fitted on the closure offers advantages in terms of assembling the device.

Other embodiments may provide a device, wherein the closure contains a seal element made from a rubber elastic material, which closes off an opening orifice of the first chamber when the closure is fitted; or wherein the closure is secured by a catch connection to prevent it from being inadvertently released, which embodiments make it easier to provide a sterile closure and prevent the chamber containing the lyophilizate from inadvertently opening.

Another embodiment provides the process of lyophilizing the substance in the first chamber.

An embodiment is disclosed wherein the outlet is connected to the closure or to the housing by an anti-tamper device; or wherein the closure is connected to the housing, the opening orifice or the glass cylinder by an anti-tamper device, such as a label, which would make it immediately obvious if the device has been manipulated because this could impair sterility.

An embodiment, wherein the housing comprises two housing parts disposed axially one behind the other and connected to one another at a connection point, and the connection point is disposed between the first chamber and the second chamber, relates to a two-part housing, and offers major advantages in terms of manufacturing and assembling the device.

A further embodiment of the invention is provided, wherein the two housing parts are connected to one another by means of a thread, they can be assembled particularly easily. Moreover, this thread connection may also be provided with an anti-tamper system, making it easy to tell whether the connection has been taken apart.

The embodiments wherein the first chamber has longitudinal grooves in the diameter towards the interior at its end remote from the front housing end make the process of lyophilizing the substance or active substance in the first chamber easy whilst preserving sterility.

As a result of the embodiment wherein the opening closed by the membrane is disposed at the end of the rear housing end, the device can be stored in a sterile environment without the operating means.

According to an embodiment wherein a coupling part is provided which can be fitted on the rear housing end, by means of which operating means are connected, and cutting or severing means are provided on the coupling part or on the operating means which pierce the membrane when the coupling part is fitted on the rear housing end, a coupling part may be used to fit the operating means.

An alternative embodiment provides operating means on the rear housing end wherein the operating means are accommodated in a protective tube which is releasably and sealingly attached to the housing and wherein the opening closed by the membrane is disposed in the protective tube, the operating means is already fitted and is accommodated in a protective tube, which again guarantees the sterility of the whole device.

Independently of the design of the device, the objective of the invention can also be achieved on the basis of the method wherein the selected method sequences not only simplify the process of lyophilizing the substance but also permit continuous processing when producing the lyophilized substance and its sterile packaging for future economic use, and the lyophilized, reconstituted substance is also easy to dispense. The excellent quality of the lyophilized substance results in an adequate shelf life and the sterility is simultaneously preserved until the time the substance is reconstituted. Another advantage of this solution resides in the fact that there are a number of options for the individual method steps, thereby offering a plurality of optional features for the device and above all resulting in a cost-effective modular system.

The objective of the invention is also independently achieved by means of a device. In addition a rapid and reliable coupling of the piston/plunger rod for operating the overall system, this solution simultaneously offers the option of a disposable device. It also offers the possibility of introducing the liquid reconstituting means for the substance into the first chamber against an appropriate over-pressure, which simultaneously rules out the risk of ingress by the reconstituted substance due to a return force acting in the direction opposite the forward direction of the piston/plunger and prevents it from escaping into the transfer set or cartridge.

The preferred embodiment of the device may be operated in steps and may further offer a possible design for the catch means.

The embodiment, wherein the catches are disposed on the terminal end of webs of the piston/plunger rod facing the interior of the housing and the piston/plunger rod regions are provided with the catch means are deformable and can elastically rebound in the direction extending radially with respect to the longitudinal mid-axis of the operating means, is preferred because the elastic deformability of the plunger rod regions produces a braking action which prevents too rapid a forward movement of the plunger rod and hence any undesirable foaming when mixing the substance with the diluent.

Another objective of the invention may also be independently achieved by a device as is provided with operating means which, when moved in the direction towards the front housing end, firstly activate the connection means so that a flow communication is established from the cartridge to the first chamber, and a cartridge stopper fitted on the rear end of the cartridge is then moved in the direction towards the front housing end so that the diluent flows out of the cartridge into the first chamber where it is mixed with the lyophilizate, and the plunger is then moved in the first chamber in the direction towards the front housing end so that the reconstituted substance is ejected out of the first chamber, wherein the connection means are retained in the interior of the housing by means of a retaining mechanism with a pre-definable retaining force.

Another embodiment of this device offers a particularly simple configuration for the retaining mechanism wherein the retaining mechanism is provided in the form. This solution ensures a specific sequence of the steps effected in the interior of the device when it is being operated.

The objective of the invention is also independently achieved by means of a device as wherein the plunger is provided with or connected to a retaining mechanism with a pre-definable retaining force in an arrangement sealing off the first chamber; as a result of this solution, a specific sequence is guaranteed for the steps which are effected in the interior of the device when it is being operated.

The particular embodiments offer options for a simple and inexpensive configuration for the retaining mechanism of the plunger, wherein the retaining mechanism is provided in the form of a brake bead disposed on the piston/plunger which has an external diameter of a bigger diameter than the internal diameter of the housing, such as for example wherein several brake beads are disposed one after the other in the direction of forward movement; or wherein the brake bead or the brake beads locate in recesses in the internal wall of the housing.

The objective of the invention is also independently achieved by a device wherein the level of the air pressure in the first chamber is selected so that it damps the forward movement of the piston/plunger in the first chamber, the piston/plunger rod is thus prevented from moving forward too quickly, thereby preventing foaming when the substance is being mixed with the diluent. Thus this type of embodiment results in a further improvement to the control of the forward feed rate.

The objective of the invention is also independently achieved by a device wherein the level of the air pressure in the first chamber is selected so that it damps the forward movement of the plunger in the first chamber. The combination of features accordingly may result in a device in which the substance or active substance is reconstituted automatically.

The objective of the invention is also independently achieved by a device wherein the connection means are retained in the interior of the housing by means of a first retaining mechanism with a pre-definable retaining force and this first retaining mechanism has a first catch position and a second catch position. The retaining mechanism improves reliability of the operations effected in sequence when the device is being operated.

The preferred embodiments may have the connection means with a second retaining mechanism which opposes a relative movement between the cartridge and the connection means by applying a pre-defined retaining force active catch means provided between the connection means and the piston/plunger, which is to prevent the connection means from being separated from the plunger, once the flow connection has been established between the cartridge and the first chamber relating to advantageous variants of the retaining mechanism which function reliably.

BRIEF DESCRIPTION OF DRAWINGS

The invention will be described in more detail below with reference to examples of embodiments illustrated in the appended drawings.

Of these:

FIGS. 4a to 4f illustrate the operating sequence which takes place when using the device illustrated in FIG. 2;

FIGS. 5a to 5f illustrate the operating sequence which takes place when using the device illustrated in FIG. 3;

FIGS. 8a to 8c is a longitudinal section through an embodiment of the device with an automatic activation system;

FIGS. 9a to 9e illustrate the operating sequence of another device.

Figure 1:
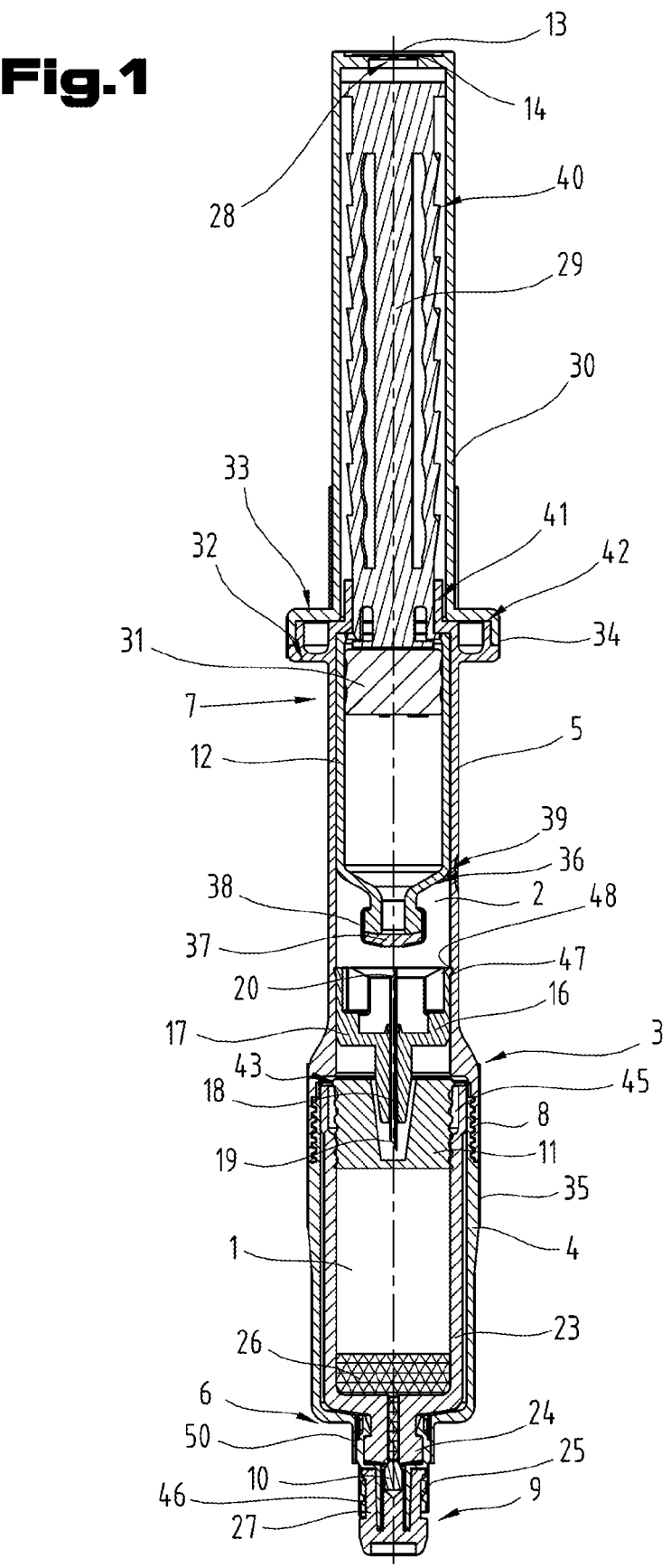
FIG. 1 is a longitudinal section through a first embodiment of the device.

Firstly, it should be pointed out that the same parts described in the different embodiments are denoted by the same reference numbers and the same component names and the disclosures made throughout the description can be transposed in terms of meaning to same parts bearing the same reference numbers or same component names. Furthermore, the positions chosen for the purposes of the description, such as top, bottom, side, etc,. relate to the drawing specifically being described and can be transposed in terms of meaning to a new position when another position is being described. Individual features or combinations of features from the different embodiments illustrated and described may be construed as independent inventive solutions or solutions proposed by the invention in their own right.

The embodiments illustrated as examples represent possible design variants of the part-feeding system and it should be pointed out at this stage that the invention is not specifically limited to the design variants specifically illustrated, and instead the individual design variants may be used in different combinations with one another and these possible variations lie within the reach of the person skilled in this technical field given the disclosed technical teaching. Accordingly, all conceivable design variants which can be obtained by combining individual details of the design variants described and illustrated are possible and fall within the scope of the invention.

FIG. 1 illustrates a first embodiment of a device proposed by the invention. A first chamber 1 containing a lyophilizate 26 is disposed in a housing 3 close to its front dispensing-side housing end 6. In the embodiment illustrated in FIG. 1, the first chamber 1 is disposed in a glass cylinder 23, which is in turn accommodated in the housing 3 made from plastic. The lyophilizate 26 was produced inside the first chamber 1, as will be explained below.

At its end disposed close to its dispensing-side, front housing end 6, the glass cylinder 23 containing the lyophilizate 26 has a tapered opening 24 on which an adapter 25 made from plastic is fitted. The plastic adapter 25 may be formed on or bonded to the glass cylinder 23 or may be attached to the glass cylinder 23 by means of a snap-fit connection.

In order to attach the adapter 25 to a cylindrical shoulder projecting out from the dispensing-side terminal end of the glass cylinder through which the opening 24 extends, this projection has a circumferentially extending groove 50 between the terminal end of the glass cylinder 23 and dispensing-side end thereof. Extending in the radial direction from the part of the adapter 25 lying at the terminal end are elastic snapper arms, which have snapper hooks projecting towards the longitudinal mid-axis of the glass cylinder into this groove 50 and the adapter is thus connected to the glass cylinder 23 so that it can not move. At its end region remote from the glass cylinder 23, the adapter 25 also has a Luer lock fitting. Naturally, it would also be possible to provide an integrally formed Luer lock fitting, in which case it would be provided with appropriate locking means for securing and retaining the closure 9 or an injection needle adjoining the adapter 25.

However, all other types of closures and fitting systems used in medical technology could naturally be provided in the region of this adapter 25.

As mentioned above, a major advantage of the device proposed by the invention and the method proposed by the invention is the fact that the injection solution, i.e. the reconstituted substance and the lyophilizate 26, can be administered free of contamination. It must be possible to guarantee this lack of contamination during the entire time the device is in use. In order to ensure or obtain these advantages, this in reality means the entire interior of the device. To this end, the seal is provided at the dispensing-side housing end 6 by means of a closure cap 27 with an integrated seal element 10 made from pharmaceutical rubber which can be snap-fitted and released again if necessary and closes off the opening of the glass cylinder 23 keeping it sealed from bacteria. In this respect, it is of advantage if the adapter 25 has a specially adapted Luer lock closure because this will prevent the closure 9 from inadvertently coming off even when the device is being handled during its ultimate use.

Seated on the adapter 25 is a closure 9, comprising a closure cap 27 made from plastic and a seal element 10 retained in it. The latter is made from pharmaceutical rubber and projects into the opening 24 in order to seal it tightly. In addition to or instead of the Luer lock fitting, the closure cap 27 is also provided with a locking shoulder 46, which prevents the closure 9 from being unintentionally removed. When the closure 9 is removed, the adapter 25 forms a Luer or a Luer lock coupling, by means of which a Luer fitting, an injection needle or tube leading to one or to some other component can be connected.

At its end opposite the dispensing end of the device, the glass cylinder 23 has bypasses 45 extending in the axial direction, which are used for the gas exchange during the lyophilisation process, as will be explained below. Fitted in this end of the glass cylinder 23 is a cylinder stopper 11 which is also made from pharmaceutical rubber and has an axial extension and can assume different positions so that it either extends beyond the length of the bypasses 45 or can be pushed into a position in which the cylinder stopper 11 tightly seals the glass cylinder 23.

Starting on the rear face of the cylinder stopper 11 remote from the first chamber 1 is a second chamber 2 in which a cartridge 12 made from glass or plastic and containing a diluent is accommodated. The cartridge 12 is closed at its dispensing-side end by mean of a cartridge sealing disc 37 made from pharmaceutical rubber which is fixedly retained on the cartridge by means of a crimped cap 38.

Seated in the rear end of the cartridge remote from the dispensing end is a cartridge stopper 31, which tightly seals the interior of the cartridge containing the diluent. Disposed between the external surface of the cartridge 12 and the internal surface of the housing 3 is at least one gas passage extending in the longitudinal direction of the housing 3. This gas passage may comprise a gap between the external diameter of the cartridge and the internal diameter of the housing or it may be provided in the form of fine longitudinal ribs or longitudinal grooves or raised areas distributed across the surface or an appropriate roughened area inside of the housing or on the outside of the cartridge. The gas passage is used for the process of sterilising the device with ethylene oxide, which will be described below.

To prevent the cartridge 12 from undesirably shifting in the direction towards the front housing end 6, at least one cartridge seating 39 is provided on the internal wall of the housing 3, on which the cartridge 12 is supported by means of its cartridge shoulders 36. It is preferable to provide several cartridge seatings 39 distributed around the circumference of the housing 3, which may be formed by softening and slightly pressing the housing wall inwards or by providing a separate component which can be inserted in the housing part.

Disposed between the cartridge sealing disc 37 and the cylinder stopper 11 is a transfer set 16, the purpose of which is to direct the diluent contained in the cartridge 12 into the first chamber 1 in order to reconstitute the lyophilizate when the device is being used. The transfer set 16 contains a continuous connecting cannula 18 contained in a cannula guide 17. The connecting cannula 18 is open in this embodiment and is therefore also open to the gas so that both sides of the transfer set 16 can be sterilized with ethylene oxide. The transfer set 16 is secured in its axial position in the housing 3 by means of resilient catch flaps 47 formed around its circumference which locate in an annular groove 48 in the rear housing part.

The housing 3 of the device may expediently comprise a front dispensing-side housing part 4 and a rear housing part 5, which are releasably screwed to one another at a connection point 8. This being the case, the connection point 8 may be covered by a label 35. This label 35 may be used as an anti-tamper system but also ensures and maintains the sterility of the entire interior of the device because if the label 35 is broken or torn, this will indicate that the housing parts 4 and 5 have been take apart from one another and that the device is no longer intact and the sterility has also not been preserved. If the rear housing part 5 is provided with a bearing surface with planes perpendicular to the longitudinal axis (flange 56 in FIG. 7), it may advantageously be used for applying and sealing a sealing film, for example.

In this case, it is sufficient if a connecting mechanism is provided in the end of the rear housing part 5 facing the plunger rod, in particular a snap-fit mechanism, by means of which the plunger rod 29 or a first of several catches 40 for coupling and fixing the plunger rod 29 to the rear housing part 5.

This connecting mechanism, which may be formed by a circumferentially extending points springing towards the longitudinal axis 4, may have elastically deformable snapper arms engaging round it and enables the plunger rod 29 to be held in position between the cartridge stopper 31 and an inwardly projecting point of the connecting mechanism and can effect a forward pushing movement on the cartridge stopper 31. In order to position the cartridge 12 at a distance so that the sealing disc 37 in the cartridge can be retained spaced apart from the tip of the connecting cannula 18 of the transfer set 16 during transport, the cartridge 12 may be connected to the rear housing part 5 by means of a press-fit seating which acts partially via the surface of the external face of the cartridge 12, or retaining elements formed by appropriate projections are provided for the cartridge around the internal surface of the rear housing part 5. In this respect, care should be taken to ensure that the retaining force of the press-fit seating or the retaining mechanisms is lower than a retaining force of the cartridge sealing disc 37 on the crimped cap 38, because the forward movement of the cartridge 12 to the point where it locates in a transfer seating 16 takes place using the medium in the cartridge 111 due to the fact that the liquid can not be compressed via the cartridge stopper 31 of the cartridge 12. In other words, the cartridge sealing disc 37 must be anchored sufficiently firmly that a forward pushing force which has to be expended by the plunger rod 20 and the cartridge stopper 31 on the cartridge in the cartridge sealing disc 37 takes place before the cartridge sealing disc 37 is pierced by the connecting cannula 18 of the transfer sets 16.

The plunger rod 29 is provided with several catches 40, the purpose of which will be explained in more detail below. A flange-type finger seating 32 is also integrally formed on the rear housing end 7. The plunger rod is accommodated in a brake cylinder shoulder 41 formed in the rear housing part 5 and is able to slide axially.

A plunger rod housing 30 which completely covers the plunger rod 29 is connected by means of a connecting flange 33 to the rear housing part 5, for example by a weld joint 42 produced by ultrasound or may be bonded or formed and which is of such a dimension that it merely serves as a breaking point and at the same time offers an additional quality criterion whereby the plunger rod housing 30 can be removed from the housing 3. A label 34 covering the connecting flange 33 and the finger seating 32 serves as a guarantee seal which, if broken, indicates that the plunger rod housing 30 has been removed from the housing 3.

Disposed terminally at its rear end, the plunger rod housing 30 has an opening 13, which is closed by a membrane 14 placed on a support lattice 28. The membrane 14 is of a type which is permeable to gas but not to bacteria. This requirement can be fulfilled by what is referred to as medical sterile paper. The purpose of the membrane 14 is to prevent the paper from being inadvertently pierced during the sterilization process and during subsequent transport prior to use.

This membrane 14 may be integrally formed in the plunger rod housing 30 or injection moulded with it and the support lattice may be pressed in, glued in, latched or secured by some other means, or may be replaced by a non-woven fabric, a woven fabric, a knitted fabric or another membrane or a filter.

The front housing part 4, the glass cylinder 23, the cylinder stopper 11 tightly sealing the glass cylinder 23 at the rear and the adapter 25 with the closure 9 fitted on it tightly closing the glass cylinder 23 at the front constitute a unit, which is produced in a closed process and can be sold as such and/or used for further processing. This unit is produced and assembled in appropriate clean rooms in order to ensure that production takes place as far as possible free of particles even prior to sterilization. The pharmaceutical rubber parts are made from a rubber formulation suitable for the lyophilization process.

This unit is pre-assembled and is so by assembling the closure 9 first of all by fitting the seal element 10 in the closure cap 27 with an assembly mechanism. The closure 9 is then connected to the adapter 25 e.g. by means of a Luer lock system so that the closure cap 27 latches in the adapter 25 by means of the locking shoulder 46 so that the two parts are firmly but releasably secured to prevent them from unintentionally coming apart.

A description will now be given of four different ways of filling the glass cylinder 23 with a substance solution and how this substance is lyophilized in the glass cylinder 23. For preparation purposes, cylinder stoppers 11 supplied ready-washed, silicone treated and sterilized as standard are introduced into a holder magazine of a filling system and stored for further processing. Alternatively, the cylinder stoppers 11 may also be washed, silicone treated, sterilized and dried in a standard filling system. In this case, the glass cylinders 23 are introduced into the filling system, silicone treated and sterilized in a hot air tunnel.

In the case of the first, second and third embodiment of the filling and lyophilization processes, the pre-treated sterile glass cylinders 23 are closed at the dispensing end—in a downstream assembly station—by means of the pre-assembled closures 9. This being the case, the adapter 25 is non-releasably latched by means of a snap-fit connection on the undercut of the glass cylinder neck 23. As a result, the opening 24 of the glass cylinder 23 is tightly sealed against bacteria by the seal element 10 of the closure 9. Closed at the dispensing end and sterile, the glass cylinders 23 are introduced into holders disposed in the filling system and the substance solution can now be metered into the open glass cylinders 23.

In the case of the first embodiment, the lyophilization process is initiated at this point and the venting or gas exchange takes place through the still open cross-sections of the glass cylinder 23. Immediately the lyophilization process ends, the cylinder stoppers 11 are automatically pushed into the glass cylinders 23 so that they are tightly sealed. In this embodiment, the bypasses 45 in the glass cylinders can be dispensed with.

In the case of the second embodiment of the filling and lyophilization processes, the pre-prepared sterile cylinder stoppers 11 are moved into position and inserted in the glass cylinders 23 exactly positioned, but only so far that the bypasses 45 of the glass cylinders 23 remain open, thereby enabling a gas exchange to take place during the subsequent lyophilization process through the open cross-sections of the bypasses 45. The lyophilization process can then be started, whereby the venting or gas exchange takes place through the still open cross-sections of the bypasses 45. As soon as the lyophilization process is complete, the cylinder stoppers 11 are automatically pushed to the end position in the glass cylinders 23 so that the bypasses 45 are tightly sealed.

In the case of the third embodiment of the filling and lyophilization processes, glass cylinders 23 without bypasses 45 are used—as was the case with the first embodiment. Again in this instance, cylinder stoppers 11 are used, the diameter of which is bigger than the internal diameter of the glass cylinders 23, and which have axially extending venting passages in their circumference. At least in the region of these venting passages, the cylinder stoppers 11 have a bigger diameter extending beyond them so that when they are pushed deeper into the chambers, the venting passages are tightly closed due to the strong compression. The cross-section of these venting passages is dimensioned so that it closes due to the elastic deformation of the cylinder stopper 11 once it is fully accommodated in the glass cylinder 23. These cylinder stoppers 11 are firstly moved into position and then inserted in the glass cylinders 23 exactly positioned but only so far that the venting passages in the cylinder stopper 11 remain open so that a gas exchange can take place during the subsequent lyophilization process through the open cross-sections of the venting passages. As soon as the lyophilization process is finished, the cylinder stoppers 11 are automatically pushed into the end position in the glass cylinders 23 so that the venting passages are compressed and thus tightly sealed.

In the case of the fourth embodiment of the filling and lyophilization processes, the glass cylinders 23 are tightly sealed at their end remote from the opening 24 with the cylinder stoppers 11 first of all ad then introduced into holders standing in the filling system with the opening 24 directed upwards. The substance solution is then metered through the opening 24 into the glass cylinders 23. During the subsequent lyophilization process, the gas exchange takes place through the opening 24 of the glass cylinder 23. Once the lyophilization process is finished, the glass cylinders 23 are closed at the dispensing end with the pre-assembled closures 9. This being the case, the adapter 25 latches on the undercut of the glass cylinder neck 23 by means of a snap-fit connection and is non-releasable. As a result, the opening 24 of the glass cylinder 23 is closed and sealed from bacteria by the seal element 10 of the closure 9.

Irrespective of which of the four embodiments is used to fill the glass cylinders 23 and run the lyophilization process, they are now closed and sealed from bacteria at both ends and can be dispatched for further processing, optionally external assembly.

The steps involved in assembling the device described below can be carried out at different times and sites from the assembly steps described so far. The finished glass cylinder 23 containing the lyophilized substance, closed and sealed from bacteria at both ends, is inserted in the front housing part 4 by means of an assembly device. During this process, ridges standing proud on the outside of the adapter 25 locate in grooves inwardly recessed into the opening shoulder of the front housing part 4. This produces a reliable coupling and optionally may prevent any twisting between the housing part 4 and the adapter 25 and the glass cylinder 23, so that the closure 9 can be removed from the device without causing a relative movement or, optionally, a relative twisting between the glass cylinder 23 and the adapter 25 or the housing part 4 can be achieved. The now completed unit, which will be referred to as an injection unit below, is now ready for further assembly.

The steps involved in assembling the device described below can also be carried out at a different time and at a different site from the assembly steps described so far.

Another unit of the device is assembled as follows. From the connection point 8, the cartridge 12 containing the diluent (water for injectable preparations) and finally the transfer set 16 are introduced into the interior at its end, e.g. through the inner, circumferentially extending collar of the tapered rear housing part 5 at its end.

At the rear end of the rear housing part 5, the plunger rod 29 is firstly introduced through the narrowed region until it latches by means of its snap-fit connection, after which the plunger rod housing 30 with the integrally formed connecting flange 33 is fitted on the finger seating 32 of the housing part 5. In addition, the join is also secured with a 4-point welded join. A label is then applied round the flange finger seating connection as evidence that the device is intact.

This unit, referred to as the activator unit, can now be connected to the injection unit described above, by screwing the rear housing part 5 onto the front housing part 4 and then likewise applying a label around the connection point 8 to provide evidence of quality assurance at this point as well.

Assembled and finished in this manner, the device can now be dispatched to a final sterilization process, during which a gas, preferably ethylene oxide, is fed to the interior of the device but does not get into the first chamber 1. The gas therefore penetrates the membrane 14 by means of which the opening 13 in the rear end of the plunger rod housing 30 is sealed from bacteria, initially arriving in the interior of the plunger rod housing, so that this interior together with the plunger rod 29 contained in it are sealed. Due to the gas exchange described above between the housing part 5 and the cartridge 12, the gas flows on to the dispensing-side end of the cartridge 12 and on through the transfer cannula 18 as far as the rear end of the cylinder stopper 11, so that all surfaces with which it comes into contact are sterilized. It goes without saying that a device of this design and sterilized in this manner does not have to be packed in special sterile packaging for storage.

Figure 2:
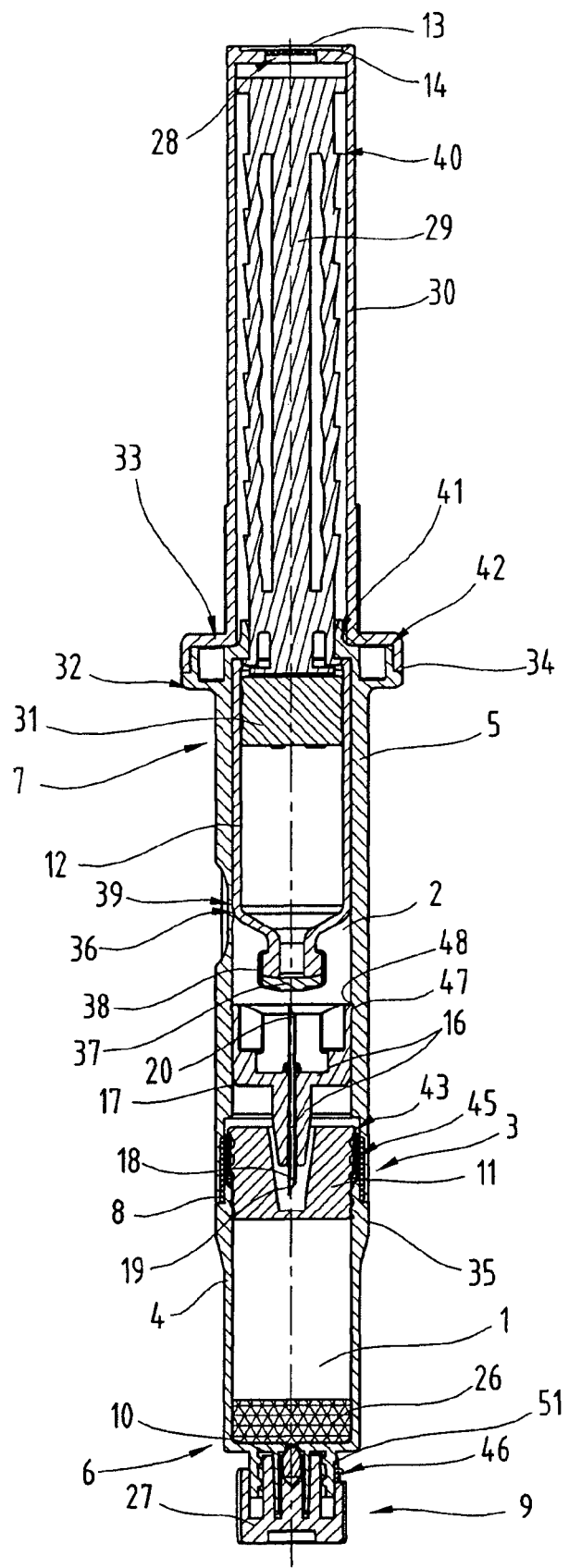
FIG. 2 is a longitudinal section through a second embodiment of the device.

FIG. 2 illustrates another embodiment of the device. The main difference from the embodiment illustrated in FIG. 1 is the fact that the first chamber is not provided in a glass cylinder but is disposed directly in the front housing part 4 made from plastic. In order to fit the closure 9, a coupling shoulder 51, preferably provided in the form of a Luer lock fitting, is formed directly on the front housing part 4. At the oppositely lying end, the first chamber 1 is sealed from bacteria, as was the case with the embodiment illustrated in FIG. 1, with a cylinder stopper 11 made from pharmaceutical rubber and here too, two different embodiments of the cylinder stopper 11 may be used, namely with or without venting passages. In the embodiment illustrated as an example in FIG. 2, bypasses 45 are provided in the front housing part 4 and the cylinder stopper 11 therefore has no venting passages.

Figure 3:
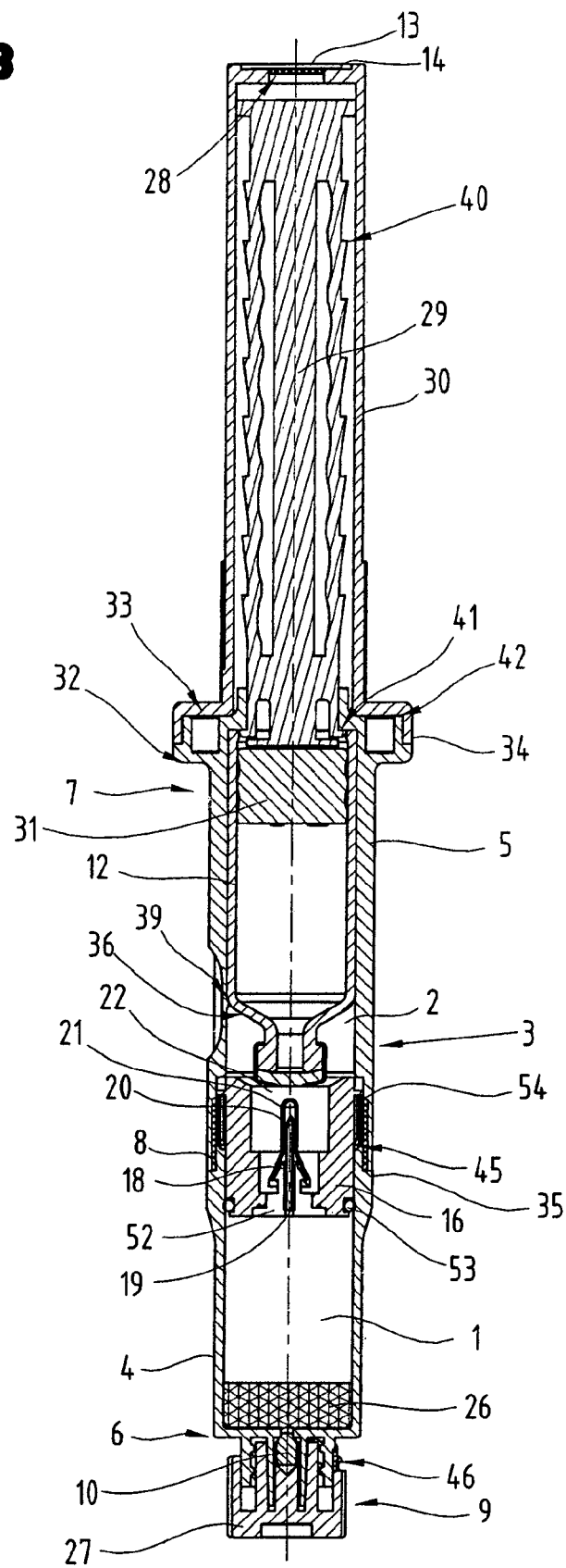
FIG. 3 is a longitudinal section through a third embodiment of the device.

The embodiment of the device illustrated in FIG. 3 is of a similar construction to that described in connection with the embodiment illustrated in FIG. 2. Here too, the first chamber 1 is disposed in the front housing part 4 made from plastic. In this embodiment, however, a different embodiment of the transfer set 16 is used and is of a design whereby the transfer set 16 constitutes the rear boundary and seal of the first chamber 1 and also assumes the function of a plunger for ejecting the reconstituted substance from the first chamber 1. Consequently, the cylinder stopper 11 described in connection with the embodiments described with reference to FIGS. 1 and 2 is not needed with this embodiment. The transfer set 16 illustrated in FIG. 3 has a connecting cannula fitting 52 in which the connecting cannula 18 is mounted and which is simultaneously used to provide a sealed fitting for a cannula protective cap 21 covering the cartridge-side cannula end 20. Unlike the transfer set 16 used with the embodiments illustrated in FIGS. 1 and 2, the dispensing-side cannula end 19 in this embodiment does not project beyond the transfer set. In order to seal the transfer set 16 in the front housing part 4, this embodiment is provided with an O-ring 53. Resilient catch flaps 47 assume the function of the brake bead 43 provided on the cylinder stopper 11 in the embodiments illustrated in FIGS. 1 and 2.

The other variants of the filling and lyophilization process described in connection with the embodiment illustrated in FIG. 1 also apply to the embodiments illustrated in FIGS. 2 and 3. The only difference is that instead of the glass cylinder 23, it is the front housing part 4 of these embodiments of the device that is filled with the substance and it is here that it is lyophilized.

The choice as to what materials should be used to make the embodiments of the device described above will primarily be taken with a view to assuring functionality in the long term and mechanical strength, even under extreme conditions. In the case of the cartridge 12, the front housing part 4, the cylinder stopper 11, the cartridge stopper 31, the cartridge sealing disc 37, the connecting cannula 18, the injection cannula 49 and all the seal elements such as O-rings, it is also necessary to use production materials which meet the requirements in force for medical products. Bearing in mind the need for sterilisation, resistance of the material to ethylene oxide is an important factor for all components, in addition to satisfying the physical requirements. For these reasons, the front housing part is preferably made from cyclic olefin copolymer, referred to below as COC. This is an amorphous thermoplastic material known under the trade name Topas 6013. The front housing part 4 of the embodiments illustrated in FIGS. 2 and 3 assumes the function of a primary packaging containing the lyophilizate. Said material was chosen for making this housing part due to the high requirements placed on it in terms of precise molding, chemical resistance, glass-type transparency, high resistance to heat forming and ultimate breaking strength, ability to withstand autoclaving at 121° C. and ability to withstand sterilization by gamma radiation and ethylene oxide. Due to its high material integrity and the fact that it is inert, COC also fulfils all the requirements placed on pharmaceutical containers for storing parenteral preparations as stipulated by EP/JP and USP including USP Class VI. Due to high processing temperatures, the absence of pyrogens can also be guaranteed. Furthermore, due to the excellent barrier afforded against water vapor, medicaments can be stored in containers for several years. As a result of the properties listed above, containers made from COC are particularly suitable for packaging biotechnical products, toxic products, diluents, lyophilizates and other pharmaceutical preparations and pharmaceutical containers made from plastic have become a genuine alternative to drug containers made from glass. Moreover, due to the molding techniques which can be used for shaping by using thermoplastic materials, the shape of the front housing part 4 can be optimally shaped and produced to the desired requirements in terms of size, venting passages (bypasses), injection head and neck, etc.

In the embodiment illustrated as an example in FIG. 1, the cartridge 12 and the first chamber 1, in other words the glass cylinder 23, are preferably made from boron silicate glass, known under the trade name of Fiolax, for example. This type of glass conforms to the requirements of the drugs formularies USP, European pharmacopoeia, Japanese pharmacopoeia and the German formulary (DAB) in terms of chemical resistance and protection from light. Conformity with the threshold limits for heavy metals (lead, cadmium, mercury, chromium VI) as stipulated by European Directive 94/62/CE is guaranteed. Glass is totally inert and provides a seal in the presence of ethylene oxide.

For reasons of mechanical stress, (spring action of the resilient catch flaps 47) a polyacetate (POM) may be used for the cannula guide 17. POM is formulated by the manufacturer for producing parts used in contact with food and conforms to the requirements of the FDA and the European Union. In the case of the plunger rod 29, as with the cannula guide, however, if the device is used in accordance with the instructions, it will not be in direct contact with the drug or with the human body. Since the cannula guide accommodates the connecting cannula 18, special emphasis was placed on choosing a material specifically formulated by the manufacturer for use in the medical product sector.

Stainless steel (NIRO 1.403, AISI 304) was selected for the connecting cannula 18. The stainless steel used is suitable and specified for making medical cannulas and is also suitable for sterilization with ethylene oxide. The connecting cannula 18 is secured in the cannula guide 17 by means of a UV-hardened cyano-acrylate adhesive, for example an adhesive such as that sold under the trade name Loctite 4304. Suitability of the adhesive for curing the cannula was also tested after sterilization in the form of a cannula seating test (strength obtained between the cannula guide 17 and connecting cannula 18) in accordance with EN ISO 7864 on the injection units. A comparison of the test results for the force needed to pull out the needle in both non-sterilized and sterilized samples exhibited no detrimental change induced by sterilization. The values measured on the sterilized samples for the pulling out force not only complied with the standard requirements laid down by EN ISO 7864 but even lay significantly above the values for the non-sterilized samples.

The selected sterilization process using ethylene oxide serves to ensure that the device as a whole is free of germs, excluding the drug (lyophilizate) packaged in a gas-tight arrangement in the first chamber 1 and the diluent (WFI) packaged in a gas-tight arrangement in the cartridge 12 contained in it. The membranes 14 and 15 acting as a barrier against bacteria are made from medical paper with a basis weight of 60 g/m². To ensure that the plunger rod housing 30 is sealed, the paper is coated with polyethylene. The material used is designed for use in the medical/pharmaceutical sector, especially for keeping substances sterile and conforms to the requirements of EN 868 Parts 1 and 7. It is readily permeable to ethylene oxide and is specified as being impermeable to bacteria.

Sterilization of the device with ETO must not result in any alteration to the lyophilizate disposed in the first chamber 1 sealed against bacteria and the diluent disposed in the cartridge 12. To ensure that this is the case, steps must be taken to ensure that no ethylene oxide is able to penetrate the interior of the first chamber 1 and the cartridge 12. In practical terms, tests were conducted to ascertain whether the syringe cylinder containing the lyophilizate and the cartridge containing the diluent (WFI) were indeed sealed against ethylene oxide by testing the cartridge contents and the contents of the first chamber 1 of the described embodiments of the sterilized devices proposed by the invention to see if they contained ethylene oxide. No evidence of ethylene oxide was found in the sterilized cartridges and first chambers. Consequently, any alteration to the diluent (water for injection purposes) and the lyophilizate due to the effect of ethylene oxide can be ruled out.

Turning to FIGS. 4a to 4f, an explanation will now be given of how the device based on the embodiment illustrated in FIG. 2 is used.

In the initial position illustrated in FIG. 4a, the activator unit is secured to the plunger rod housing 30 and the connection between the activator unit and the injection unit (rear housing part 5) still has the label 34 affixed.

In the position illustrated in FIG. 4b, the plunger rod housing 30 has been removed from the rear housing part 5 and the device can now be activated in the manner described below.

In the position illustrated in FIG. 4c, the device is activated by a plunger rod movement initiated by applying a light pressure to the plunger rod 29. This pressure is transmitted to the cartridge stopper 31. Since the cartridge is tightly sealed and filled with a liquid diluent, the cartridge stopper 31 can not be pushed into the cartridge 12. Consequently, the cartridge 12 is released against the resistance of the cartridge seating 39 out of the non-operating position and moved in the direction of the transfer set 16. As a result, the resilient catch flaps 47 of the transfer set 16 are released from the annular groove 48 of the housing part 5 and the transfer set 16 is pushed in the direction of the cylinder stopper 11 until it sits against the cylinder stopper 11. As this happens, the connecting cannula 18 integrated in the transfer set 16 pierces the cylinder stopper 11 and penetrates the interior of the first chamber 1. The other end of the connecting cannula 18 therefore also pierces the cartridge sealing disc 37 of the cartridge 12 and the connecting cannula 18 penetrates the interior of the cartridge 12, so that a continuous connection is then established between the cartridge interior (containing the diluent) and the first chamber 1 (containing the lyophilizate).

One of the catches 40 of the plunger rod 29 then automatically locates in the rear housing part 5 and secures the transfer set 16 so that it is connected to the cylinder stopper 11 in this position. It is no longer possible to pull the plunger rod back out of this position. As a result, the connection between the first chamber 1 containing the lyophilizate and the cartridge containing the diluent via the connecting cannula 18 is maintained.

As the plunger rod movement continues from the position illustrated in FIG. 4c to that illustrated in FIG. 4d, the diluent is transferred form the cartridge 12 through the connecting cannula 18 into the first chamber 1 due to the pressure on the cartridge stopper 31 and the lyophilizate is therefore slowly dissolved. The counter-pressure which occurs as the diluent is transferred, generated by the compression of the air cushion in the first chamber 1, causes a braking effect so that the diluent is not transferred too quickly, thereby preventing excessive foaming of the drug solution. An additional braking effect is created by the resistance of the resilient catches 40 of the plunger rod 29 against the resistance of the brake cylinder shoulder 41 in the rear housing part 5. Another catch 40 locates in the rear housing part 5 and holds the cartridge 12 together with the transfer set 16 firmly in this position against the internal pressure (air cushion) generated in the first chamber 1. As a result of this barrier, the injection solution is reliably prevented from flowing back into the cartridge. Once the position illustrated in FIG. 4d is reached, the device is shaken lightly to check whether the lyophilizate has fully dissolved. The closure 9 can then be removed, after which the device is held with its dispensing-side end 6 upwards so that the air pressure builds up in the first chamber 1 without the injection solution escaping. Once an injection cannula 49 has been fitted and the first chamber 1 has been vented by it, the device is now ready for administering an injection. This position is illustrated in FIG. 4e.

During the injection, the injection solution is forced out of the first chamber 1 by the cylinder stopper 11. Once the injection has been administered, the device finally reaches the position illustrated in FIG. 4f. Another catch 40 then locates in the housing part 5 and secures the plunger rod 29 in its end position to prevent it from being pulled out. This effectively prevents the device from being used again.

The sequences described above in connection with FIGS. 4a to 4f take place in exactly the same way using a device illustrated in FIG. 2 and a device illustrated in FIG. 1. The sequences which take place in the case of a device illustrated in FIG. 3 will be explained below with reference to FIG. 5.

In the initial position illustrated in FIG. 5a, the activator unit is secured to the plunger rod housing 30 and the connection between the activator unit and the injection unit (rear housing part 5) is still provided with the anti-tamper closure (label 34).

In the position illustrated in FIG. 5b, the plunger rod housing 30 has already been removed from the rear housing part 5 and the device can now be activated. By applying a light pressure to the plunger rod 29, the system is activated by the plunger rod movement. The pressure on the cartridge stopper 31 causes the cartridge 12 to be released from the non-operating position against the resistance of the cartridge seating 39 and moved in the direction of the transfer set 16.

During the transfer from the position illustrated in FIG. 5b to the position illustrated in FIG. 5c, the cannula protective cap 21 is compressed and the sterile connecting cannula 18 pierces the cartridge sealing disc 37 and penetrates the interior of the cartridge 12 (containing the diluent). The transfer set 16 thus remains in position, secured by the integrally formed brake lugs 54. The catch 40 of the plunger rod 29 then automatically locates in the rear housing part 5 and locks the transfer set 16 so that it is connected to the connecting cannula 18 and the cartridge 12, in the position illustrated in FIG. 5c. The plunger rod can no longer be moved back out of this position.

As the plunger rod continues to move due to the pressure on the cartridge stopper 31, the diluent is transferred from the cartridge 12 through the connecting cannula 18 into the first chamber 1 and the lyophilizate slowly dissolves. Once the diluent has been transferred into the first chamber 1, another catch 40 of the plunger rod 29 automatically locates in the rear housing part 5 and locks the cartridge 12, together with the transfer set 12, in the position illustrated in FIG. 5d. As result of this lock, the injection solution can no longer flow back into the first chamber 1 due to the pressure which has been generated.

Once the lyophilizate has been fully reconstituted, the closure 9 is removed and the injection cannula 49 is fitted (FIG. 5e). When the first chamber 1 has been vented via the cannula, the injection can be administered. To this end, the brake lugs 54 which have until now been holding the transfer set 16 in a shoulder in the front housing part 4 are moved away and the transfer set 16 starts to move towards the dispensing end of the device. The transfer set 16 is now used as a syringe plunger and forces the injection solution out of the first chamber 1.

Once the injection has been administered, the device is finally in the position illustrated in FIG. 5f, in which another catch 40 locates in the housing part 5 and locks the plunger rod 29 in its end position, preventing it from being pulled out. This effectively prevents the device from being used again.

Figure 6:
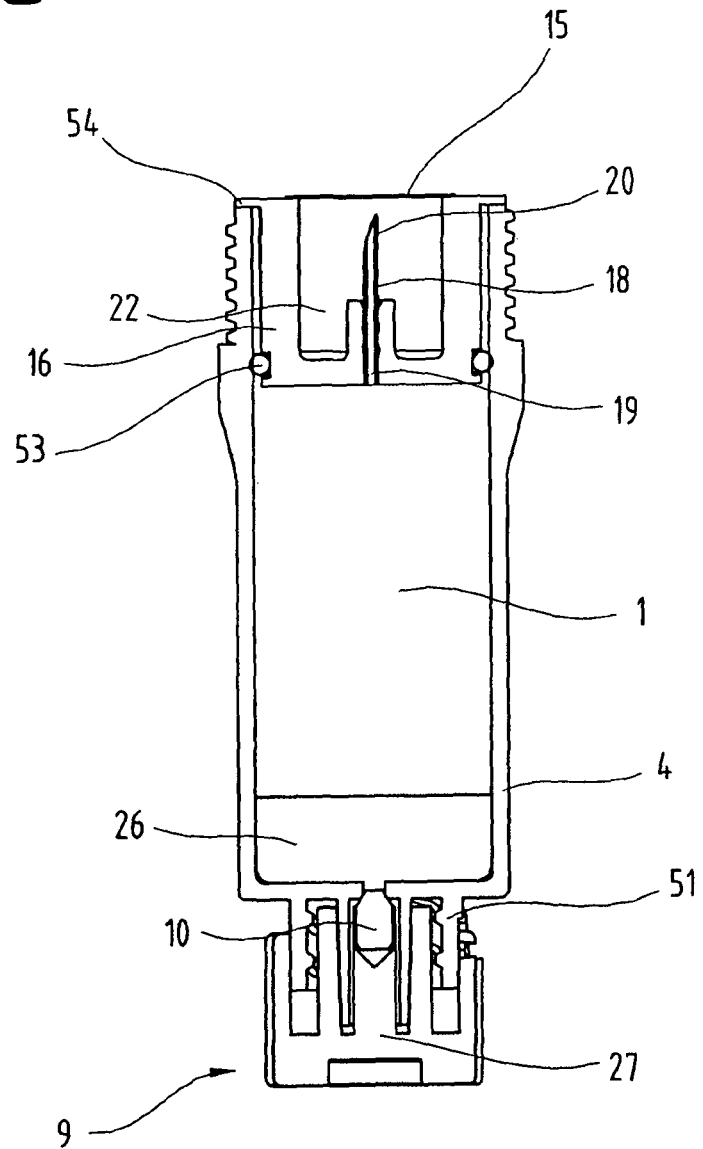
FIG. 6 is a longitudinal section through an embodiment of the injection unit.

FIG. 6 illustrates an embodiment of an injection unit, which is manufactured, stored and sold separately and can subsequently be assembled with an activator part. As with the embodiments described with reference to FIGS. 2 and 3, the first chamber 1 of this embodiment containing the lyophilizate 26 is formed directly by the front housing part 4 and has a coupling shoulder 51 at the dispensing end forming a Luer lock fitting and releasably secures the closure 9 comprising the closure cap 27 with the seal element 10 disposed in it. Fitted at the oppositely lying end of the housing part 4 is a transfer set 16, which differs from the transfer set illustrated in FIG. 3 due to the fact that a recess 22 is provided in which the cartridge-side end 20 of the connecting cannula 18 is disposed, the latter being closed by a membrane 15 providing a seal against ingress by bacteria from outside. The membrane 15 is made from medical sterile paper and is coated with polyethylene for this purpose and tightly welded to the transfer set 16. As with the example illustrated in FIG. 3, the transfer set 16 is sealed by means of an O-ring 53 in the front housing part 4 and secured in the illustrated position by means of the brake lugs 54. When assembled with an activator unit, the membrane 15 initially remains intact. Not until the device is activated and, more specifically, the cartridge 12 is pushed forwards as described in connection with FIGS. 5b and 5c, is the membrane 15 pierced by the cartridge 12.

Figure 7:
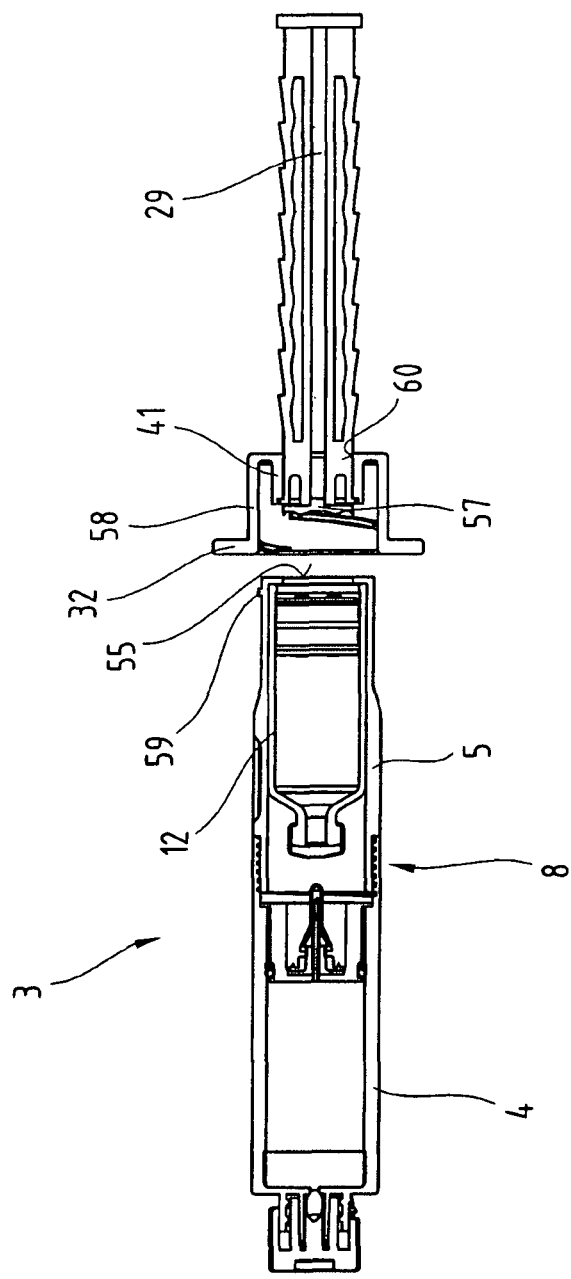
FIG. 7 is a longitudinal section through another embodiment of the device.

Another embodiment of the device is illustrated in FIG. 7. As with the embodiments described in connection with FIGS. 1 to 3, the housing 3 comprises the front housing part 4 and the rear housing part 5 containing the cartridge 12, which are screwed together at the connection point 8. Integrally formed on the rear end of the rear housing part 5 is a flange 56 projecting radially inwards. A membrane 55 made from medical sterile paper with a coating of polyethylene is welded onto it in a sealing arrangement. This results in an injection unit sealed against bacteria. FIG. 7 illustrates an activator unit comprising a coupling part 58 bearing the plunger rod 29. It has a finger seating 32 and can be connected to the rear housing part 5 by means of a bayonet coupling 59. As with the embodiments described above, the plunger rod 29 is guided in a brake cylinder shoulder 41. Provided on the rear end of the brake cylinder shoulder 41 are catch means 60 comprising inwardly projecting catch lugs which project into notches provided in the plunger rod 29 and ensure that a certain amount of force must be applied in order to push the plunger rod 29. Cutting means 57 are disposed on the end of the plunger rod 29 which sever the 55 as soon as the activator unit is connected to the rear housing part 5 by means of the bayonet coupling 59.

FIGS. 8a to 8c illustrate another embodiment of the device in which activation takes place automatically on the basis of a spring force. The device essentially corresponds to that illustrated in FIG. 2, except that the rear end of the plunger rod housing 30 is of a different design, as will be described below. Connected to the open, rear end of the plunger rod housing 30 by means of a welded, screwed or snap-fit connection 65 is a spring housing 63. In its interior is a push rod 66, which widens in a plate-type arrangement at its front end and has two catch hooks 67 at its rear end. The rear end of the spring housing 63 accommodates a catch plate 68 with an orifice in which the catch hooks 67 sit in the initial position illustrated in FIG. 8a. A spring 64 sits on the push rod 66 and is biased between its dish-type extension and the catch plate 68. At the end, the spring housing 63 is closed by an end cap 69 which has a central opening 70. In the initial position illustrated in FIG. 8a, a locking cap 61 is fitted on the end cap, which has a central locking pin 62 which extends through the opening 70 of the end cap 69 and between the catch hooks 67. Due to the locking pin 62, the catch hooks 67 are prevented from moving towards one another and thus slipping through the opening in the catch plate. As a result, the device is locked in this position illustrated in FIG. 8a and can not be released. A label (not illustrated) may be applied to the transition between the locking cap 61, the end cap 69 and the spring housing 63 serving as a guarantee seal. It is also possible to use a single continuous label to protect the connection points between the rear housing part 5 and the plunger rod housing 30, between the plunger rod housing 30 and the spring housing 63 as well as between the spring housing 63, the end cap 69 and the locking cap 61.

In preparation for use, the locking cap 61 is firstly pulled off, as indicated by the arrow in FIG. 8a. The activation system of the device can then be triggered. This is done by pushing the end cap in the direction towards the dispensing end of the device. As a result, the conical opening 70 disposed in the end cap 69 pushes the catch hooks 76 towards one another so that they move through the opening of the catch plate 68 under the force of the biased spring 64. As may be seen by comparing FIGS. 8a and 8b, the end cap 69 moves along an axial path in order to trigger the device. FIG. 8b illustrates a position corresponding to the injection unit in the position illustrated in FIG. 4d. This means that the piston rod or plunger rod 29 has moved so far under the force of the spring 64 that the lyophilizate in the first chamber 1 has been reconstituted with the diluent which has flown out of the cartridge 12 into the first chamber 1 and—after venting the first chamber—is ready to be administered. Naturally, the spring 64 is dimensioned so that its force is strong enough to overcome the resistance afforded by the gas cushion in the first chamber 1 and the mutual friction between the moving components of the device. As with the embodiments described above, catches 40 on the plunger rod 29 also prevent the plunger rod 29 from being moved back.

The plunger rod housing 30 together with the spring housing and the components contained in it can now be removed from the device, as indicated by the arrow in FIG. 8c.

To enable this embodiment of the device to be sterilized with ethylene oxide, a membrane with a sealed opening (not illustrated) may be provided in the casing of the plunger rod housing 30, in the casing of the spring housing 63 or in the locking cap 61.

FIGS. 9a to 9e illustrate the use of another embodiment of the device proposed by the invention. The device is of a similar design to the device described above with reference to FIG. 1, the main differences of which will be explained below.

The device has a housing comprising a front housing part 4 and a rear housing part 5 and the front housing part 4 is fitted with a glass cylinder 23 containing the lyophilisate 26. At its injection dispensing end, the glass cylinder 23 is provided with an adapter 71, which engages in the groove 50 of the glass cylinder 23. Seated on the adapter 71 is a closure 72, which closes and seals the glass cylinder 23. Disposed between the external face of the adapter 71 and the internal face of the neck of the front housing part 4 is an O-ring 73. This structure enables the closed glass cylinder 23 containing the lyophilizate 26 and incorporating the adapter 71 and closure 72 to be inserted in the front housing part 4. During the sterilization process with ethylene oxide, the latter is able to move forward due to the clearance between the front housing part 4 and the glass cylinder 23 as far as the O-ring 73, which keeps the entire interior sealed and sterile.

The transfer set 75 differs from the transfer set 16 illustrated in FIG. 1 due to the fact that, in addition to outer resilient catch lugs 76 co-operating with the internal wall of the rear housing part 5, it also has inner resilient catch lugs 74 co-operating with the cartridge head. In the initial position illustrated in FIG. 9a, the cartridge 12 sits with the cartridge head on inner resilient catch lugs 74 of the transfer set 75. The outer resilient catch lugs 76 of the transfer set 75 are locked in a first catch position, for example by means of an annular groove 77 in the rear housing part 5, in this position.

The outer and inner resilient catch lugs are therefore dimensioned so that the force needed to overcome the braking action of the outer resilient catch lugs 76 is within a range of 1 to 1.5 Newton, for example, and thus lower than the force needed to overcome the braking effect of the inner resilient catch lugs, which is in the order of approximately 2 Newton, for example.

Starting from the position illustrated in FIG. 9a, the plunger rod housing 30 is firstly removed so that the plunger rod is free and can be operated. At the start of operation, the plunger rod 29 pushes on the cartridge stopper 31 and thus pushes the cartridge 12 with the transfer set 75 forward by the distance 79. As a result, the outer resilient catch lugs 76 of the transfer set 75 are forcibly released from the annular groove 77 and during the forward movement latch in the annular groove 78 of the rear housing part 5 again.

At the same time, the cylinder stopper 11 is pierced by the connecting cannula 18, which moves by a distance 80 corresponding to the distance 79 so that the front cannula tip now stands inside the first chamber 1 of the glass cylinders 23. The needle shoulder part 81 of the transfer set 75 therefore closes the conical opening 82 of the cylinder stopper 11. Provided on the needle shoulder part 81 are spring elements, which locate in the conical opening 82 of the cylinder stopper 11 during this step and thus connect the transfer set 75 to the cylinder stopper 11. In particular, this prevents the transfer set 75 from being removed from the cylinder stopper 11 again and liquid therefore flows into the space between the rear housing part 5 and the cartridge 12. The position now reached, illustrated in FIG. 9b, is locked by the latching of a catch 40 of the plunger rod 29.

During the ongoing motion sequence from the position illustrated in FIG. 9b to the position illustrated in FIG. 9c, the braking force of the inner resilient catch lug 74, which is lower than the force by which the cylinder stopper 11 is seated in the glass cylinder 23, is overcome and the cartridge 12 moves relative to the transfer set 75 by the distance 83 until it sits with the cartridge head tightly against the base of the transfer set 75. Accordingly, the rear tip of the connecting cannula 18 pierces the cartridge sealing disc 37 seated in the cartridge head so that the transfer of the diluent through the connecting cannula 18 into the first chamber 1 is now initiated. The connection between the connecting cannula 18 and the cartridge 12 in this position is locked by another catch 40 of the plunger rod 29.

During the ongoing motion sequence from the position illustrated in FIG. 9c into the position illustrated in FIG. 9d, the plunger rod 29 is slowly pushed further. The catches 40 of the plunger rod 29 and the fact that they are guided in the brake cylinder shoulder produces a braking action, thereby preventing the plunger rod 29 from being moved forwards too fast. After covering the distance 84, a perceptible increase in resistance indicates that the position illustrated in FIG. 9d has been reached and the diluent has been transferred from the cartridge 12 into the first chamber 1. The lyophilizate 26 is dissolved in the first chamber 1. As the diluent flows into the first chamber 1, a pressure builds in it, which, in conjunction with the braking effect of the plunger rod catch system described above, counteracts too rapid an injection of the diluent, largely preventing any foaming as the diluent is transferred to the first chamber 1. The position of the cylinder stopper 11 in the first chamber 1 connected to the transfer set 75 is locked in this instance by a plunger rod catch 40. Once the substance (drug) has been reconstituted, the injector is lightly shaken and the solution checked for particles as a safety precaution.

In the position illustrated in FIG. 9d, the first chamber 1 now contains the reconstituted substance 85 and air 86. The syringe at this instant must be held so that the closure 72 is at the top. Only then is the closure 72 removed from the syringe and the injection cannula 49 fitted. The sterility of the syringe and the injection solution is guaranteed until the point when the injection cannula 49 is fitted. Once the injection cannula 49 has been fitted, the air is forced out and the requisite quantity of solution is injected due to the movement by the distance 87. To enable only a partial quantity of the substance 85 to be injected if necessary, a scale 88 is provided on the glass cylinder 23 or on the front housing part 4. Once the quantity of solution has been injected, the relevant locking catch 40 of the plunger rod 29 automatically locates in the cartridge housing 3 and locks the plunger rod 29 in the end position. As a result, it is no longer possible to carry out a manipulation (extraction of the plunger rod) with the syringe.

Figure 9E:
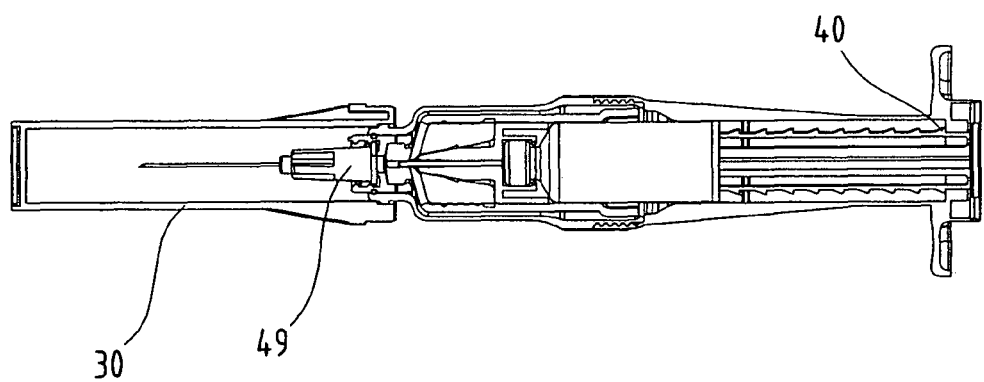

In order to prevent injuries by the contaminated injection needle 49 after administering the injection, the plunger rod housing 30 is simply placed on the front housing part 4 by means of the cannula 49, as illustrated in FIG. 9e, and latches so that it can not be released again. The injector, which is now closed at both ends and can no longer be manipulated, can now be disposed of without any problem and without any risk of injury.

For the sake of good order, finally, it should be pointed out that in order to provide a clearer understanding of the structure of the device, it and its components are illustrated to a certain extent out of scale and/or on an enlarged scale and/or on a reduced scale.

The underlying objectives of the invention and the independent solutions proposed by the invention may be found in the description.

Above all, the individual features illustrated in the embodiments shown in the drawings may be construed as independent solutions proposed by the invention in their own right. The associated objectives and solutions proposed by the invention may be found in the detailed descriptions of the drawings.

LIST OF REFERENCE NUMBERS

1 First chamber
2 Second chamber
3 Housing
4 Front housing part
5 Rear housing part
6 Front end 3
7 Rear end 3
8 Connection point 4-5
9 Closure
10 Seal element in 9
11 Cylinder stopper/plunger 12 Cartridge
13 Opening
14 Membrane in 13
15 Other membrane
16 Connection means
17 Cannula guide
18 Connecting cannula
19 Cannula end dispensing side
20 Cannula end cartridge side
21 Cannula protective cap
22 Recess
23 Glass cylinder
24 Opening 23
25 Adapter
26 Lyophilisate
27 Closure cap
28 Support lattice
29 Piston rod or Plunger rod
30 Piston or Plunger rod housing
31 Cartridge stopper
32 Finger seating
33 Connecting flange
34 Label round 33
35 Label round 4+5
36 Cartridge shoulder
37 Cartridge sealing disc
38 Crimped cap on 12
39 Cartridge seating
40 Catches
41 Brake cylinder shoulder
42 Weld joint at 33
43 Brake bead on 11
44 Brake web
45 Bypasses
46 Locking shoulder on 27
47 Resilient catch flaps
48 Annular groove
49 Injection cannula
50 Groove in 23
51 Coupling shoulder
52 Connecting cannula fitting
53 O-ring
54 Brake lugs
55 Membrane
56 Flange
57 Cutting means
58 Coupling part
59 Bayonet coupling
60 Catch means
61 Locking cap
62 Locking pin
63 Spring housing
64 Spring
65 Connection
66 Push rod
67 Catch hook
68 Catch plate
69 End cap
70 Opening
71 Adapter
72 Closure
73 O-ring
74 Inner resilient catch lugs
75 Transfer set
76 Outer resilient catch lugs
77 Annular groove
78 Annular groove
79 Distance
80 Distance
81 Needle shoulder part
82 Conical opening in 11
83 Distance
84 Distance
85 Substance
86 Air
87 Distance
88 Scale

What is claimed is:

1. A device for containing and reconstituting a lyophilized substance, and for administering the reconstituted substance, the device comprising:
a single elongate housing, including:
a dispensing-side front housing end and a rear housing end disposed opposite the dispensing-side front housing end;
a first chamber containing a lyophilizate and being provided or formed in the housing in the region of said front housing end, said first chamber being tightly sealed at an end facing said front housing end by a removable closure and being tightly sealed at an end in the direction of said rear housing end by a piston/plunger;
a second chamber provided or formed in the housing in the region of said rear housing end;
at least one opening connecting said second chamber to ambient atmosphere and being closed by a membrane permeable to gas but not to bacteria;
a cartridge containing a diluent and being disposed in said second chamber and being tightly sealed at an end remote from the front housing end by a cartridge stopper displaceable in said cartridge;
connection means disposed between the first chamber and the cartridge to establish a connection between the interior of the cartridge and the first chamber; and
an operating means configured to co-operate with the cartridge stopper and being disposed on said rear housing end, said operating means including a plunger rod that is slideable along an axial direction of said rear housing, the cartridge stopper also being movable in the rear housing along the axial direction toward the front housing end in cooperation with movement of the plunger rod along the axial direction, said operating means being provided with a catch means extending substantially the length of the operating means and permitting movement of said plunger rod towards the front housing end only while preventing movement of said plunger rod in the opposite direction,
wherein an initial sliding movement of the plunger rod along the axial direction towards the front housing end causes transfer of the diluent from the cartridge into the first chamber and reconstitution of the lyophilizate, and a further sliding movement of the plunger rod along the axial direction towards the front housing end causes the reconstituted lyophilizate to move out of the first chamber.

2. The device as claimed in claim 1, wherein the cartridge stopper is disposed on the side of the membrane facing the first chamber and at a close distance to the membrane.

3. The device as claimed in claim 2, wherein the cartridge stopper is disposed at a distance of 0.1 to 30 mm from the membrane.

4. The device as claimed in claim 2, wherein the cartridge stopper is disposed at a distance of 0.1 to 5 mm from the membrane.

5. The device as claimed in claim 1, wherein the volume of the first chamber is greater than the volume of the lyophilized substance.

6. The device as claimed in claim 1, wherein the air pressure in the first chamber is higher than 1 bar or ambient air pressure.

7. The device as claimed in claim 1, wherein the air pressure in the first chamber is lower than 1 bar or ambient air pressure.

8. The device as claimed in claim 1, wherein the connection means comprise a cannula guide displaceable in the housing, and in which a connecting cannula having one cannula end directed towards the plunger and one cannula end directed towards the cartridge is accommodated, and the connecting cannula is a double-ended needle which can be secured by its middle region in the cannula guide and is retained by gluing, forming or by a press-fit seating.

9. The device as claimed in claim 1, wherein the connection means comprises a connecting cannula which is accommodated in the plunger at one cannula end, and the other cannula end is directed towards the cartridge.

10. The device as claimed in claim 9, wherein the cannula end directed towards the cartridge is covered by a cap made from a rubber elastic material and the cap is connected to the piston/plunger in a sealed arrangement.

11. The device as claimed in claim 9, wherein the cannula end directed towards the cartridge disposed in a recess of the piston/plunger, and the recess is closed by another membrane which is permeable to gas but not to bacteria.

12. The device as claimed in claim 1, wherein the first chamber is formed by a glass cylinder which is in turn accommodated in the housing.

13. The device as claimed in claim 1, wherein the single elongate housing has a tapered opening at the dispensing-side front housing end, which supports an adapter fitted on the removable closure.

14. The device as claimed in claim 1, wherein the removable closure contains a seal element made from a rubber elastic material, and which closes off an opening orifice of the first chamber when the removable closure is fitted.

15. The device as claimed in claim 1, wherein the removable closure is secured by a catch connection that prevents the removable closure from being inadvertently released.

16. The device as claimed in claim 1, wherein the removable closure has an outlet communicating with the interior of the first chamber which can be closed and through which air can pass but not liquids.

17. The device as claimed in claim 16 wherein the outlet can be closed to prevent ingress by bacteria.

18. The device as claimed in claim 16, wherein the outlet is connected to the removable closure or to the housing by an anti-tamper device.

19. The device as claimed in claim 1, wherein the removable closure is connected to the housing, the opening orifice or the glass cylinder by an anti-tamper device.

20. The device as claimed in claim 1, wherein the single elongated housing comprises front and rear housing parts disposed axially one behind the other and connected to one another at a connection point disposed between the first chamber and the second chamber, the front housing part extending from the dispensing-side front housing end to the connection point, and the rear housing part extending from the connection point to the rear housing end.

21. The device as claimed in claim 20, wherein the connection point is provided in the form of a threaded connection.

22. The device as claimed in claim 21, wherein the connection point is secured by an anti-tamper device.

23. The device as claimed in claim 22, wherein the plunger is made from a rubber elastic material and has a bigger diameter than the internal diameter of the first chamber and has at least one axially extending venting passage disposed in the region of the circumference of the piston/plunger, the cross-section of which is dimensioned so that it is closed by the elastic deformation of the plunger when the plunger is fully accommodated in the first chamber.

24. The device as claimed in claim 1, wherein the first chamber has longitudinal grooves in the diameter towards the interior at the end remote from the front housing end.

25. The device as claimed in claim 1, wherein the opening closed by the membrane is disposed at the end of the rear housing end.

26. The device as claimed in claim 1, wherein a coupling part is provided which can be fitted on the rear housing end, by which the operating means is connected, and cutting or severing means are provided on the coupling part or on the operating means which pierces the membrane when the coupling part is fitted on the rear housing end.

27. The device as claimed in claim 26, wherein biased spring means are provided which cause the movement of the operating means when the biased spring means is relaxed.

28. The device as claimed in claim 1, wherein the operating means are accommodated in a protective tube which is releasably and sealingly attached to the housing.

29. The device as claimed in claim 28, wherein the opening closed by the membrane is disposed in the protective tube.

30. The device as claimed in claim 29, wherein the connection means is dimensioned so that whilst the operating means is being moved in the direction towards the front housing end, the connection means is first operated so that a flow connection is established from the cartridge to the first chamber, the cartridge stopper is then moved in the direction towards the front housing end so that the diluent flows from the cartridge into the first chamber where it is mixed with the lyophilizate, and the plunger in the first chamber is then moved in the direction towards the front housing end so that the reconstituted substance is ejected from the first chamber.

31. The device as claimed in claim 30, wherein the catch means includes a plurality of catches disposed one immediately after the other in the direction of movement of the operating means.

32. The device as claimed in claim 31, wherein the catch means are provided in the form of a catch pawl arrangement.

33. The device as claimed in claim 32, wherein the operating means comprises a piston/plunger rod with deformable webs extending along it which can elastically rebound in the direction extending radially with respect to the longitudinal mid-axis of the piston/plunger rod, and the catch means has catches formed on the terminal end of the webs facing the internal face of the housing.

34. The device as claimed in claim 33, wherein the connection means are retained in the interior of the housing by a first retaining mechanism in the housing with a pre-defined retaining force.

35. The device as claimed in claim 34, wherein the first retaining mechanism is provided in the form of a groove in the internal wall of the housing and extending around at least a part of the circumference, and catch arms are disposed on the connection means and biased in the direction of the internal wall of the housing with catch projections located in the groove.

36. The device as claimed in claim 34, wherein the first retaining mechanism has a first catch position and a second catch position.

37. The device as claimed in claim 36, wherein the connection means has a second retaining mechanism which opposes a relative movement between the cartridge and the connection means by applying a pre-defined retaining force.

38. The device as claimed in claim 37, wherein active catch means are provided between the connection means and the piston/plunger and which prevent the connection means from being separated from the plunger once the flow connection has been established between the cartridge and the first chamber.

39. The device as claimed in claim 1, wherein the piston/plunger is provided with or connected to a retaining mechanism with a pre-defined retaining force in an arrangement sealing off the first chamber.

40. The device as claimed in claim 39, wherein the retaining mechanism is provided in the form of a brake bead disposed on the piston/plunger and which has an external diameter of a bigger diameter than the internal diameter of the housing.

41. The device as claimed in claim 40, wherein several brake beads are disposed one after the other in the direction of forward movement.

42. The device as claimed in claim 41, wherein the brake bead one or more of the brake beads are located in recesses in the internal wall of the housing.

43. A method of containing a substance in a device as claimed in claim 1, the method comprising:
  (i) sealing tightly the end of the first chamber lying opposite the dispensing end by the piston/plunger;
  (ii) filling this first chamber with a substance through the dispensing-end opening;
  (iii) lyophilizing said substance in the chamber; and
  (iv) tightly sealing said dispensing-end opening using the removable closure.

\* \* \* \* \*